US 6,746,666 B1

(12) United States Patent
Luther

(10) Patent No.: US 6,746,666 B1
(45) Date of Patent: Jun. 8, 2004

(54) MICROPIGMENT MIXTURE

(75) Inventor: Helmut Luther, Grenzach-Wyhlen (DE)

(73) Assignee: Ciba Specialty Chemicals Corporation, Tarrytown, NY (US)

(*) Notice: Subject to any disclaimer, the term of this patent is extended or adjusted under 35 U.S.C. 154(b) by 106 days.

(21) Appl. No.: 10/018,199

(22) PCT Filed: Jun. 8, 2000

(86) PCT No.: PCT/EP00/05314

§ 371 (c)(1),
(2), (4) Date: Dec. 14, 2001

(87) PCT Pub. No.: WO00/78277

PCT Pub. Date: Dec. 28, 2000

(30) Foreign Application Priority Data

Jun. 18, 1999 (EP) .............................. 99810543

(51) Int. Cl.$^7$ ............................ A61K 7/42; A61K 7/44; A61K 7/00; A61K 3/53
(52) U.S. Cl. ................ 424/59; 424/60; 424/400; 424/401; 514/241
(58) Field of Search ............................ 424/59, 60, 400, 424/401; 514/241

(56) References Cited

U.S. PATENT DOCUMENTS

| 5,338,539 | A | 8/1994 | Raspanti | 424/59 |
| 5,445,815 | A | 8/1995 | Siegfried | 424/59 |
| 5,601,811 | A | 2/1997 | Gallagher et al. | 424/709 |
| 5,760,111 | A | 6/1998 | Birbaum et al. | 524/100 |
| 6,193,960 | B1 | 2/2001 | Metzger et al. | 424/59 |
| 6,495,122 | B2 * | 12/2002 | Fankhauser et al. | 424/59 |

FOREIGN PATENT DOCUMENTS

| EP | 0582189 | 2/1994 |
| EP | 0821939 | 2/1998 |
| WO | 97/00851 | 1/1997 |

OTHER PUBLICATIONS

W. Rabb et al., Pflegekosmetik, Wissenschaftliche Verlagsgesellschaft mgH Stuttgart 1999, pp. 260–272.

Dr. U. Scöffling, Trier, Arzneiformenlehre, DAV, Stuttgart 1998, pp. 70–73.

* cited by examiner

Primary Examiner—Shelley A. Dodson
(74) Attorney, Agent, or Firm—Kevin T. Mansfield

(57) ABSTRACT

The use of mixtures of micronised organic UV filters in protecting human and animal skin and hair against the damaging effect of UV readiation and the use thereof in cosmetic and pharmaceutical formulations are described.

The micronised mixtures used according to the invention cover a broad UV spectrum and therefore exhibit excellent sunscreen properties.

26 Claims, No Drawings

MICROPIGMENT MIXTURE

The present invention relates to the use of mixtures of micronised organic UV filters in protecting human and animal skin and hair against the damaging effect of UV radiation and to their use in cosmetic and pharmaceutical formulations.

It is known that certain organic UV filters, for example sparingly soluble benzotriazole or triazine compounds, exhibit pronounced UV filtering properties when they are in the form of single compounds in micronised form. By virtue of their specific, substance-typical properties, however, they only ever absorb, reflect or scatter a certain portion of the damaging UV range.

There is strong interest in light-protective filters that cover a broad UV spectrum and thus offer better UV protection.

The aim of the present invention is therefore to find micronised organic UV filters that cover a broader portion of the UV range, with which it is thus possible to achieve better UV protection.

It has now been found, surprisingly, that mixtures of at least two micronised UV filters are able to achieve that aim.

The present invention therefore relates to the use of mixtures of micronised organic UV filters in protecting human and animal skin and hair against the damaging effect of UV radiation.

UV filters suitable for use according to the invention are organic, in some cases sparingly soluble, compounds, for example triazine derivatives, especially hydroxyphenyltriazine compounds or benzotriazole derivatives, amides containing a vinyl group, cinnamic acid derivatives, sulfonated benzimidazoles, Fischer base derivatives, diphenylmalonic acid dinitriles, oxalyl amides, camphor derivatives, diphenyl acrylates, para-aminobenzoic acid (PABA) and derivatives thereof, salicylates, benzophenones and further classes of substances known as UV filters.

Preferred triazine derivatives suitable for use according to the invention correspond to formula

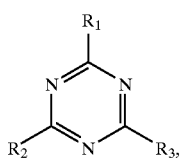

(1)

wherein $R_1$, $R_2$ and $R_3$ are each independently of the others hydrogen; OH; $C_1$–$C_{18}$alkoxy; —$NH_2$; —NH—$R_4$; —N($R_4$)$_2$; —O$R_4$, $R_4$ is $C_1$–$C_5$alkyl; phenyl; phenoxy; anilino; pyrrolo, wherein phenyl, phenoxy, anilino and pyrrolo are unsubstituted or may be substituted by one, two or three OH groups, carboxy, —CO—$NH_2$, $C_1$–$C_5$alkyl or $C_1$–$C_5$alkoxy; a methylidene-camphor group; a group of formula —(CH═CH)$_m$C(═O)—O$R_4$; a group of formula

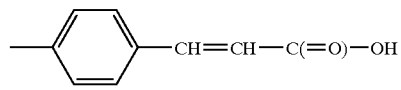

or a corresponding alkali metal, ammonium, mono-, di- or tri-$C_1$–$C_4$alkylammonium, mono-, di- or tri-$C_2$–$C_4$alkanolammonium salt, or a $C_1$–$C_3$alkyl ester thereof; or a radical of formula

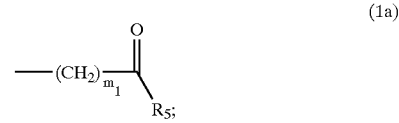

(1a)

$R_5$ is hydrogen; $C_1$–$C_5$alkyl unsubstituted or substituted by one or more OH groups; $C_1$–$C_5$alkoxy; amino; mono- or di-$C_1$–$C_5$alkylamino; M; a radical of formula

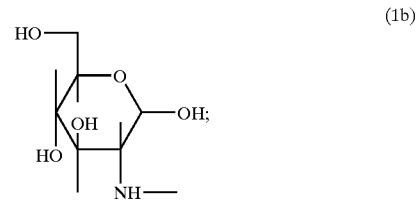

(1b)

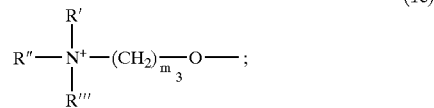

(1c)

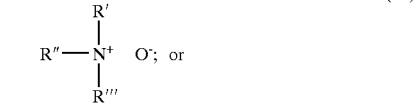

(1d)

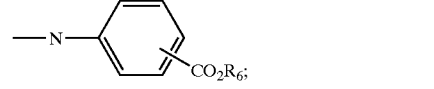

(1e)

wherein

R', R" and R'" are each independently of the others $C_1$–$C_{14}$alkyl unsubstituted or substituted by one or more OH groups;

$R_6$ is hydrogen; M; $C_1$–$C_5$alkyl; or a radical of formula —(CH$_2$)$_{m_2}$—O—$T_1$;

M is a metal cation;

$T_1$ is hydrogen; or $C_1$–$C_8$alkyl;

m is 0 or 1;

$m_2$ is from 1 to 4; and $m_3$ is from 2 to 14.

Further preferred triazine derivatives suitable for use according to the invention correspond to formula

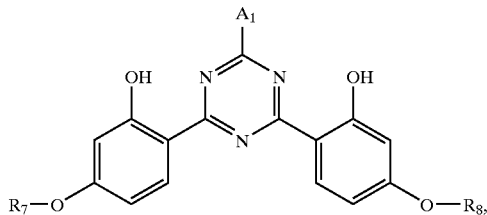

(2)

wherein $R_7$ and $R_8$ are each independently of the other $C_1$–$C_{18}$alkyl; $C_2$–$C_{18}$alkenyl; a radical of formula —$CH_2$—$CH(-OH)$—$CH_2$—O—$T_1$; or $R_7$ and $R_8$ are a radical of formula

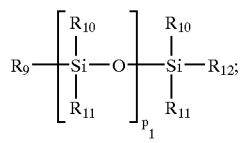

(2a)

$R_9$ is a direct bond; a straight-chain or branched $C_1$–$C_4$alkylene radical or a radical of formula —$C_{m_1}H_{2m_1}$—O—;

$R_{10}$, $R_{11}$ and $R_{12}$ are each independently of the others $C_1$–$C_{18}$alkyl; $C_1$–$C_{18}$alkoxy or a radical of formula

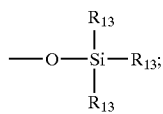

$R_{13}$ is $C_1$–$C_5$alkyl;
$m_1$ is from 1 to 4;
$p_1$ is from 0 to 5;
$A_1$ is a radical of formula

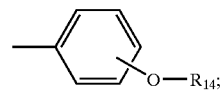

(2b)

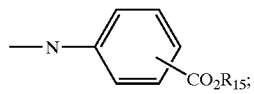

(2c)

or of formula

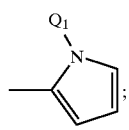

(2d)

$R_{14}$ is hydrogen; $C_1$–$C_{10}$alkyl, —$(CH_2CHR_{16}$—O$)_{n_1}$— $R_{15}$; or a radical of formula —$CH_2$—$CH(-OH)$— $CH_2$—O—$T_1$;

$R_{15}$ is hydrogen; M; $C_1$–$C_5$alkyl; or a radical of formula —$(CH_2)_{m_2}$—O—$(CH_2)_{m_3}$—$T_1$;

$R_{16}$ is hydrogen; or methyl;
$T_1$ is hydrogen; or $C_1$–$C_8$alkyl;
$Q_1$ is $C_1$–$C_{18}$alkyl;
M is a metal cation;
$m_2$ and $m_3$ are each independently of the other from 1 to 4; and
$n_1$ is from 1 to 16.

Very especially preferred triazine derivatives of formula (2) correspond to formulae

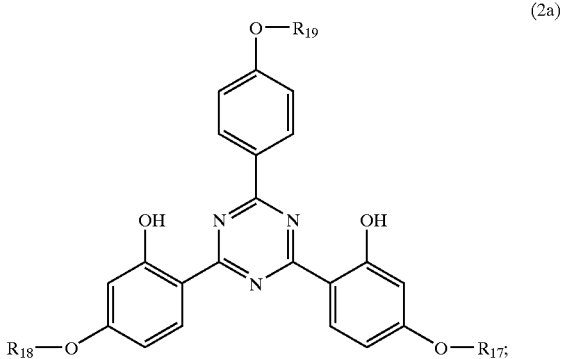

(2a)

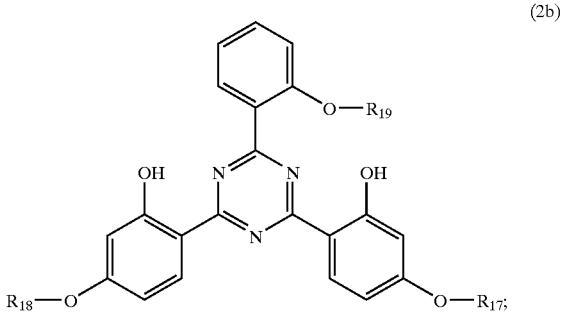

(2b)

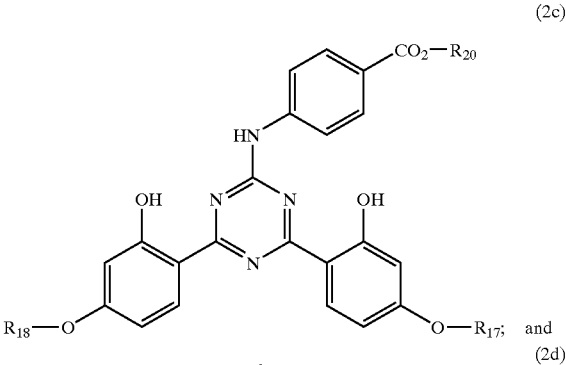

(2c)

and

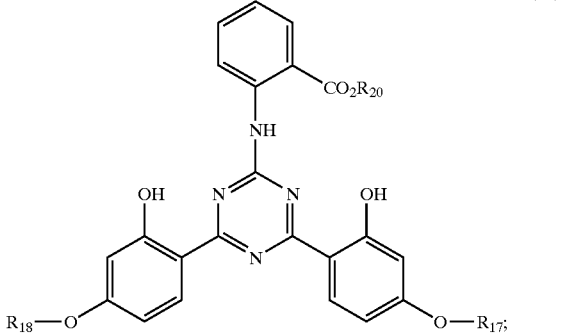

(2d)

wherein

R$_{17}$ and R$_{18}$ are each independently of the other C$_3$–C$_{18}$alkyl; or —CH$_2$—CH(—OH)—CH$_2$—O—T$_1$;

R$_{19}$ is C$_1$–C$_{10}$alkyl or a radical of formula

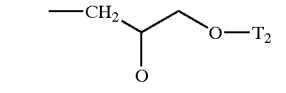
(2a$_1$)

or

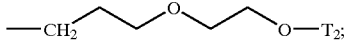
(2a$_2$)

R$_{20}$ is hydrogen; M; C$_1$–C$_5$alkyl; —NH—C$_1$–C$_5$alkyl; preferably —NH-tert-alkyl; or a radical of formula —(CH$_2$)$_m$—O—T$_2$;

T$_1$ and T$_2$ are each independently of the other hydrogen; or C$_1$–C$_5$alkyl; and m is from 1 to 4.

Of very special interest are compounds of formulae (2a) and (2b) wherein

R$_{17}$ and R$_{18}$ are each independently of the other C$_1$–C$_{18}$alkyl; or —CH$_2$—CH(—OH)—CH$_2$—O—T$_1$;

R$_{19}$ is C$_1$—C$_{10}$alkyl;

and compounds of formulae (2c) and (2d) wherein

R$_{17}$ and R$_{18}$ are each independently of the other C$_1$–C$_{18}$alkyl or —CH$_2$—CH(—OH)—CH$_2$—O—T$_1$; and T$_1$ is hydrogen; or C$_1$–C$_5$alkyl.

Of very great interest are triazine compounds of formulae (2a)–(2d) wherein

R$_{17}$ and R$_{18}$ have the same meaning.

Further interesting triazine compounds suitable for use according to the invention correspond to formula

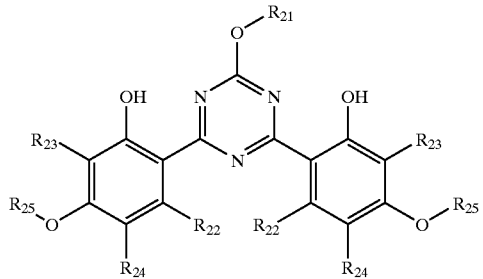
(3)

wherein

R$_{21}$ is C$_1$–C$_{30}$alkyl; C$_2$–C$_{30}$alkenyl; C$_5$–C$_{12}$cycloalkyl unsubstituted or mono or poly-substituted by C$_1$–C$_5$alkyl; C$_1$–C$_5$alkoxy-C$_1$–C$_{12}$alkyl; amino-C$_1$–C$_{12}$alkyl; C$_1$–C$_5$-monoalkylamino-C$_1$–C$_{12}$alkyl; C$_1$–C$_5$dialkylamino-C$_1$–C$_{12}$alkyl; a radical of formula

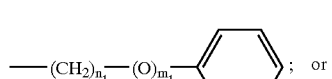
(3a)

or

(3b)

wherein

R$_{22}$, R$_{23}$ and R$_{24}$ are each independently of the others hydrogen, —OH; C$_1$–C$_{30}$alkyl, C$_2$–C$_{30}$alkenyl, R$_{25}$ is hydrogen; or C$_1$–C$_5$alkyl;

m$_1$ is 0 or 1; and n$_1$ is from 1 to 5.

Preferred compounds correspond to formula

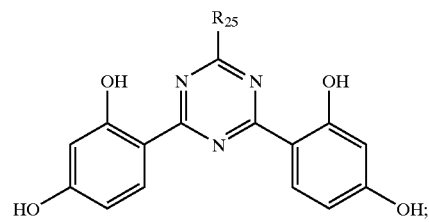
(4)

wherein

R$_{26}$ is

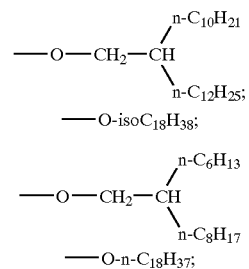

or —O-2-ethylhexyl; —O—(CH$_2$)$_3$—N(C$_2$H$_5$)$_2$;

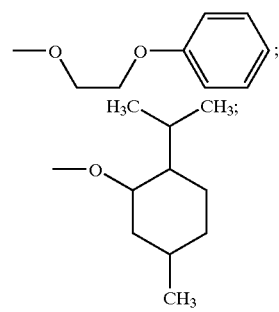

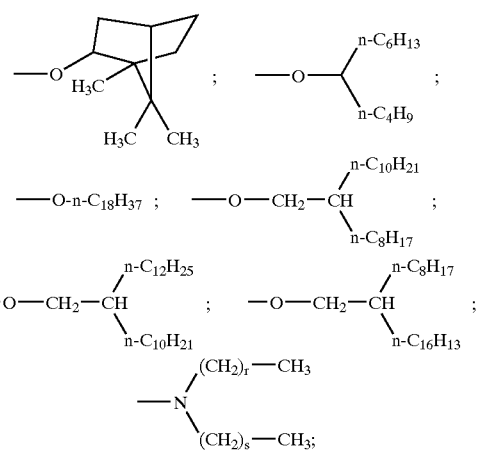

and r and s are each independently of the other from 0 to 20.

Examples of triazine derivatives suitable for use according to the invention correspond to the formulae

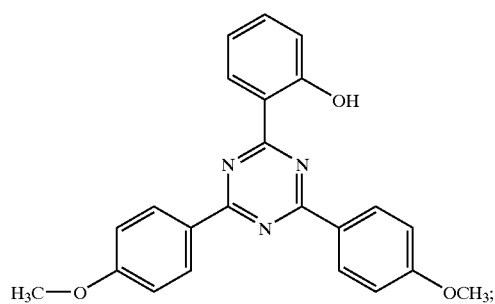
(5)
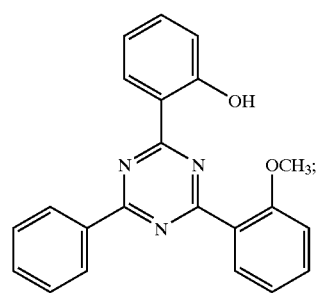
(6)
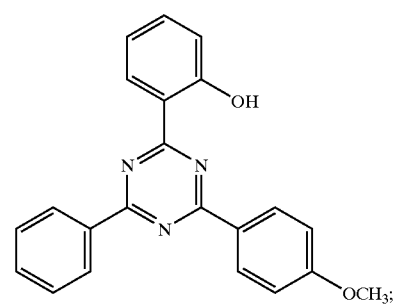
(7)
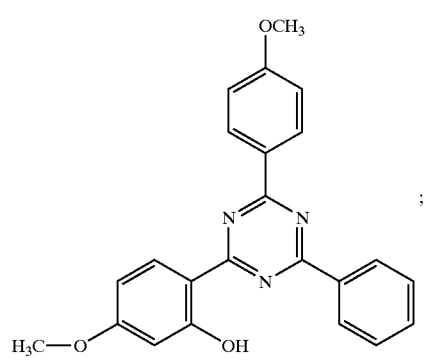
(8)
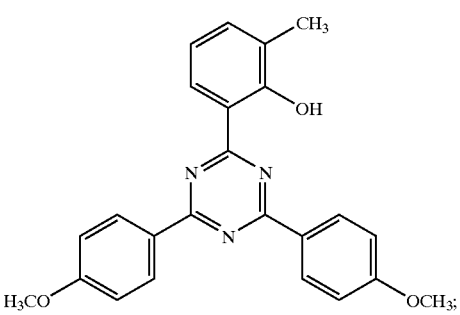
(9)
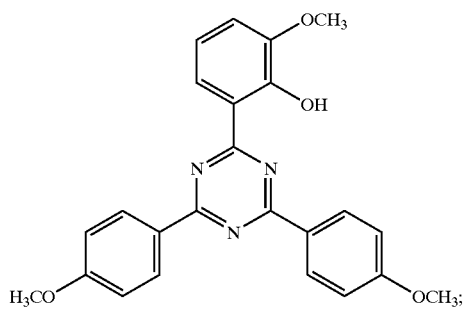
(10)
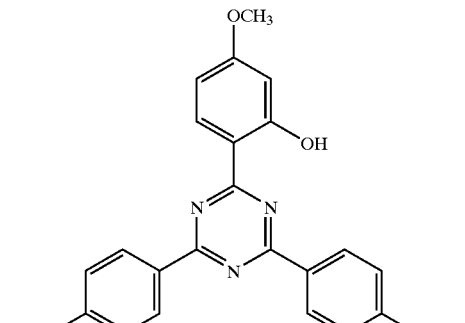
(11)
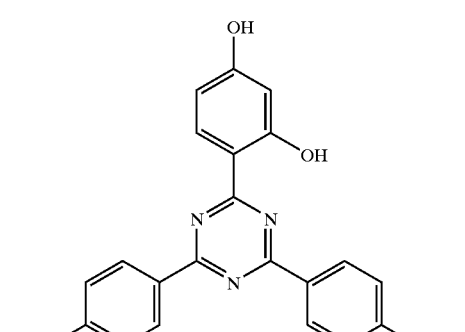
(12)
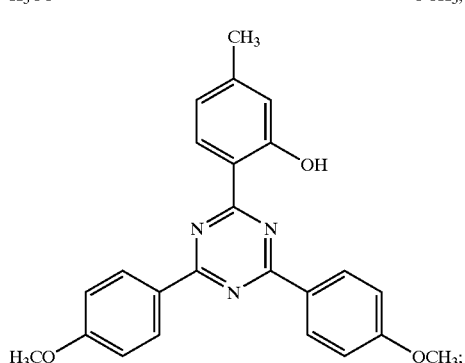
(13)
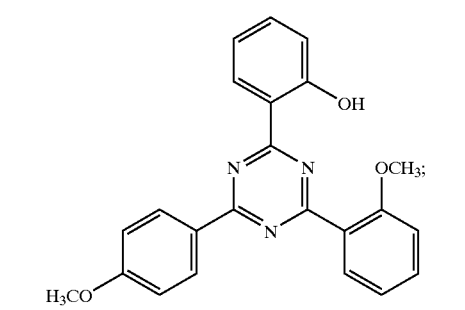
(14)

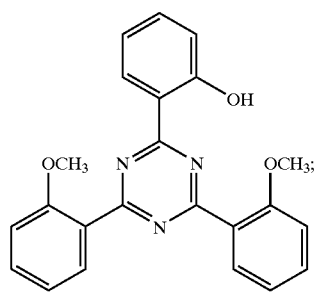
(15)
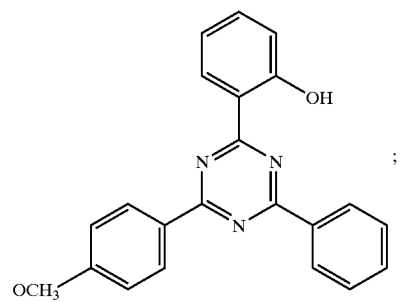
(16)
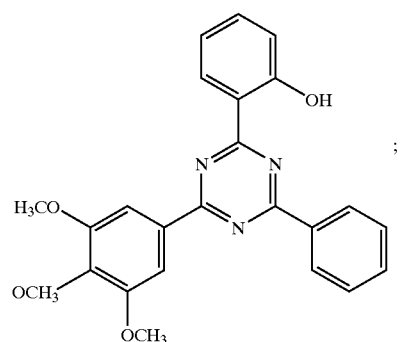
(17)
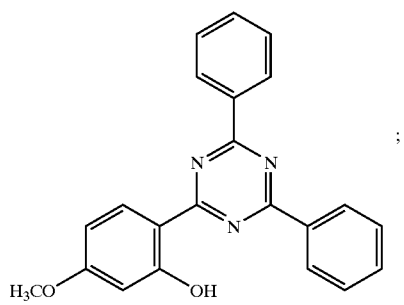
(18)
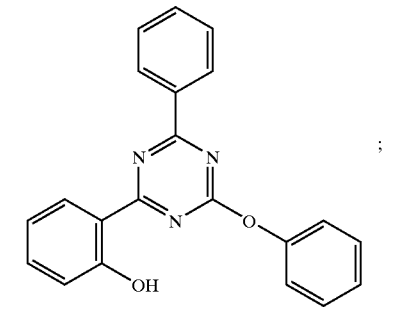
(19)
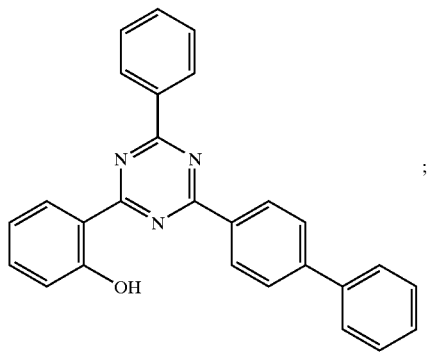
(20)
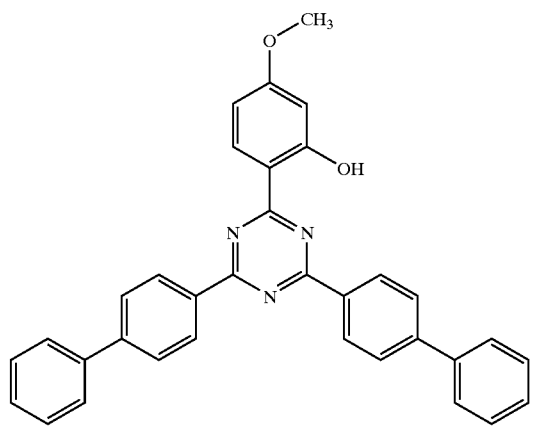
(20a)
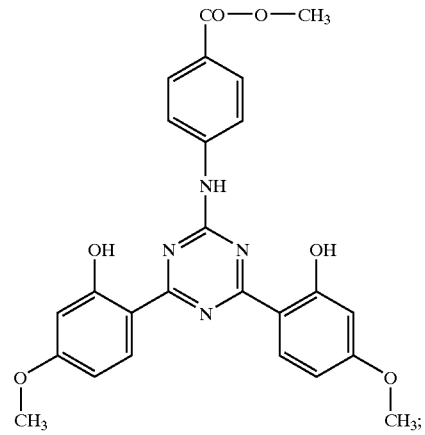
(21)
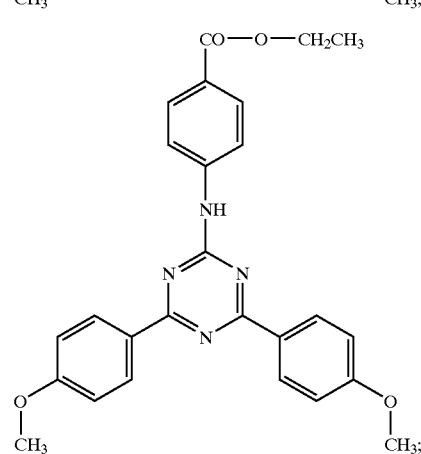
(22)

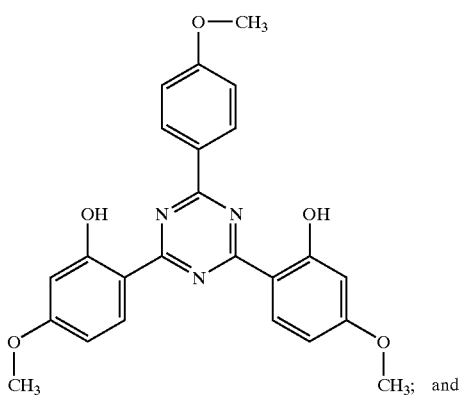
(23)

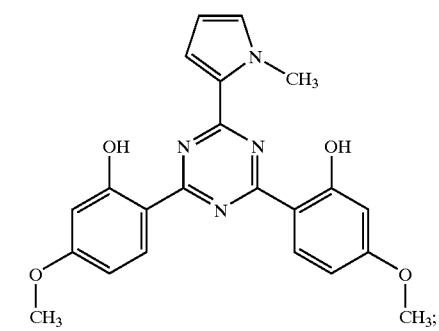
(24)

also 2,4,6-tris(diisobutyl-4'-aminobenzalmalonate)-s-triazine and 2,4-bis(diisobutyl-4-amino-benzalmalonate)-6-(4'-aminobenzylidenecamphor)-s-triazine.

Triazine compounds suitable for use according to the invention that are likewise preferred are described in EP-A-654 469, e.g. the compound of formula

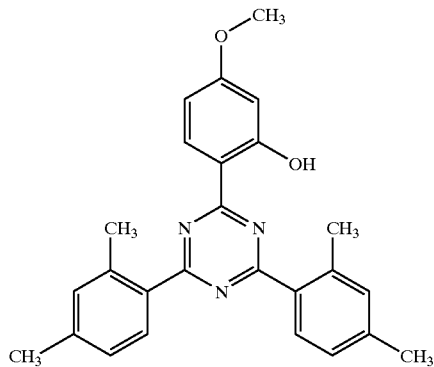
(24a)

Triazine compounds especially suitable for use according to the invention are described, for example, in EP-A-0 818 450, e.g. the compound of formula

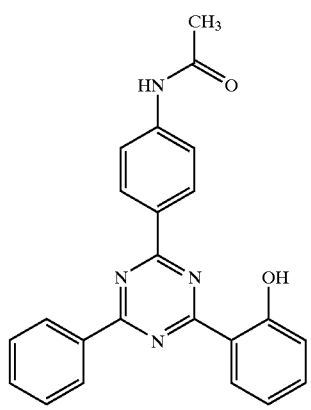
(24b)

Very especially preferred triazine derivatives suitable for use according to the invention correspond to formula

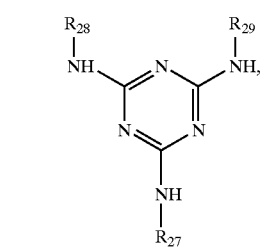
(25)

wherein $R_{27}$, $R_{28}$ and $R_{29}$ are each independently of the others a radical of formula

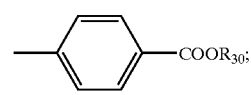
(25a)

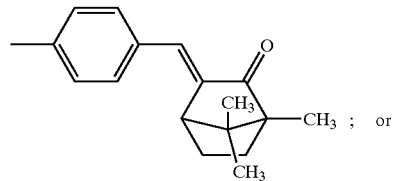
(25b)

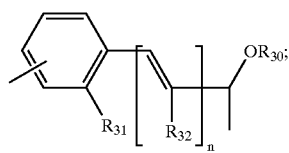
(25c)

or $R_{30}$ is hydrogen; an alkali metal; an ammonium group $-N(R_{33})_4$, $R_{33}$ is hydrogen, $C_1$–$C_5$alkyl; or a polyoxyethylene radical that has from 1 to 10 ethylene oxide units and the terminal OH group can be etherified with a $C_1$–$C_5$alcohol;

$R_{31}$ is hydrogen; —OH; or $C_1$–$C_6$alkoxy;

$R_{32}$ is hydrogen or —COOR$_{30}$; and n is 0 or 1.

When $R_{30}$ is an alkali metal, it is especially potassium or more especially sodium. $(R_{33})_4$ is especially a mono-, di- or tri-$C_1$–$C_4$alkylammonium salt, a mono-, di- or tri-$C_2$–$C_4$alkanol-ammonium salt or a $C_1$–$C_3$alkyl ester thereof.

When $R_{33}$ is a $C_1$–$C_3$alkyl group, it is especially a $C_1$–$C_2$alkyl group, more especially a methyl group, and when $R_{33}$ is a polyoxyethylene radical, that radical contains especially from 2 to 6 ethylene oxide units.

Preferred benzotriazole compounds suitable for use according to the invention correspond to formula

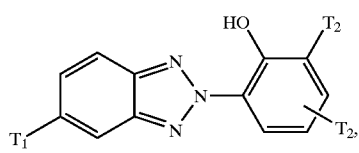

(26)

wherein $T_1$ is $C_1$–$C_5$alkyl or preferably hydrogen; and $T_2$ is $C_1$–$C_5$alkyl, preferably tert-butyl, or phenyl-substituted $C_1$–$C_4$alkyl, especially α,α-dimethylbenzyl.

A further preferred class of benzotriazole compounds suitable for use according to the invention corresponds to formula

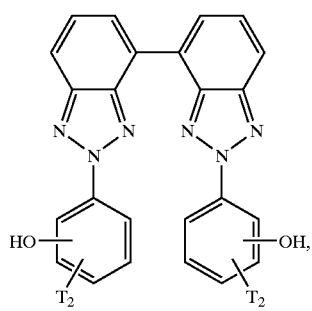

(27)

wherein $T_2$ is as defined for formula (26).

Further, especially preferred benzotriazole compounds suitable for use according to the invention correspond to formula

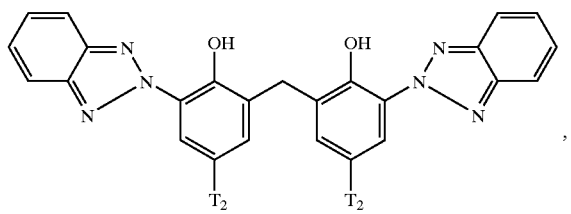

(28)

wherein $T_2$ is as defined for formula (26) and is preferably methyl, tert-butyl or iso-octyl.

Preferred vinyl-group-containing amides suitable for use according to the invention correspond to formula

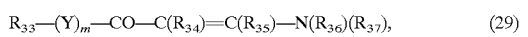

(29)

wherein $R_{33}$ is $C_1$–$C_5$alkyl, preferably methyl or ethyl, or phenyl unsubstituted or substituted by one, two or three of the radicals OH, $C_1$–$C_5$alkyl, $C_1$–$C_5$alkoxy and CO—OR$_{33}$;

$R_{34}$, $R_{35}$, $R_{36}$ and $R_{37}$ are each independently of the others $C_1$–$C_5$alkyl, preferably methyl or ethyl; or hydrogen;

Y is —NH or —O—; and m is as defined above.

Preferred compounds of formula (29) are 4-methyl-3-penten-2-one, ethyl 3-methylamino-2-butenoate, 3-methylamino-1-phenyl-2-buten-1-one and 3-methylamino-1-phenyl-2-buten-1-one.

Preferred cinnamic acid amides suitable for use according to the invention correspond to formula

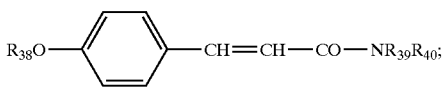

(30)

wherein $R_{38}$ is hydrogen or $C_1$–$C_5$alkoxy, preferably methoxy or ethoxy;

$R_{39}$ is hydrogen or $C_1$–$C_5$alkyl, preferably methyl or ethyl; and $R_{40}$ is —(CONH)$_m$-phenyl, wherein m is as defined above and the phenyl group is unsubstituted or substituted by one, two or three of the radicals OH, $C_1$–$C_3$alkyl, $C_1$–$C_3$alkoxy and CO—OR$_{30}$.

$R_{40}$ is preferably phenyl, 4-methoxyphenyl or the phenylaminocarbonyl group.

Further preferred cinnamic acid derivatives are 2-ethylhexyl-4-methoxy-cinnamate or -isoamylate or inter alia the cinnamic acid derivatives disclosed in U.S. Pat. No. 5,601,811 and WO 97/00851.

Preferred sulfonated benzimidazoles suitable for use according to the invention correspond to formula

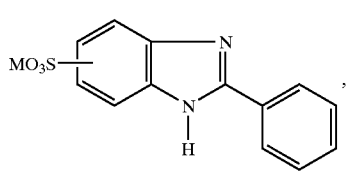

(31)

wherein

M is hydrogen or an alkali metal, preferably sodium, an alkaline earth metal, e.g. magnesium or calcium, or zinc.

Preferred Fischer base aldehydes suitable for use according to the invention correspond to formula

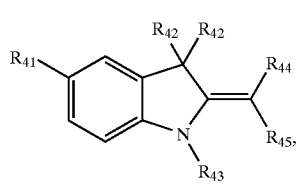

(32)

wherein $R_{41}$ is hydrogen; $C_1$–$C_5$alkyl; $C_1$–$C_{18}$alkoxy; or halogen;

$R_{42}$ is $C_1$–$C_8$alkyl; $C_5$–$C_7$cycloalkyl; or $C_6$–$C_{10}$aryl;
$R_{43}$ is $C_1$–$C_{18}$alkyl or a radical of formula

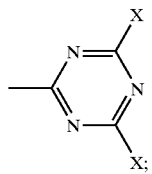 (32a)

$R_{44}$ is hydrogen; or a radical of formula

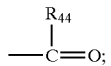

$R_{45}$ is

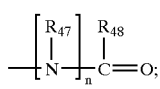

$C_1$–$C_{18}$alkoxy: or a radical of formula

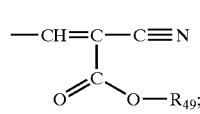 (32b)

$R_{46}$ and $R_{47}$ are each independently of the other hydrogen; or $C_1$–$C_5$alkyl;
$R_{48}$ is hydrogen; $C_1$–$C_5$alkyl; $C_5$–$C_7$cycloalkyl; phenyl; phenyl-$C_1$–$C_3$alkyl;
$R_{49}$ is $C_1$–$C_{18}$alkyl;
X is Hal; a radical of formula

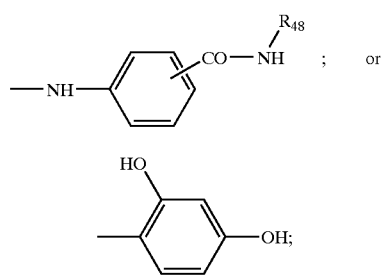 (32c)

(32d)

and
n is 0; or 1.
Further compounds that can preferably be used correspond to formula

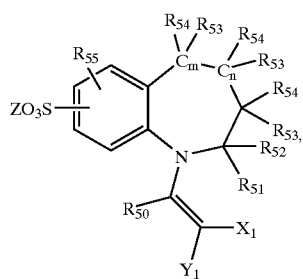 (33)

wherein
$R_{50}$, $R_{51}$, $R_{52}$, $R_{53}$, $R_{54}$ are each independently of the others hydrogen, $C_1$–$C_8$alkyl or $C_5$–$C_{10}$-cycloalkyl;

$R_{55}$ is hydrogen; $C_1$–$C_8$alkyl; $C_5$–$C_{10}$cycloalkyl; hydroxy; $C_1$–$C_8$alkoxy; $COOR_{56}$; or $CONR_{57}R_{58}$;
$R_{56}$, $R_{57}$ and $R_{58}$ are each independently of the others hydrogen or $C_1$–$C_6$alkyl;
X and Y are each independently of the other hydrogen, —CN; $CO_2R_{59}$; $CONR_{59}R_{60}$; or $COR_{59}$; it being possible for the radicals X and Y additionally to be a $C_1$–$C_8$alkyl radical, a $C_5$–$C_{10}$alkyl radical, especially phenyl, or a heteroaryl radical having 5 or 6 ring atoms, it also being possible for X and Y or
$R_{50}$ together with one of the radicals X and Y to be the radical for completing a 5- to 7-membered ring which may contain up to 3 hetero atoms, especially oxygen and/or nitrogen. it being possible for the ring atoms to be substituted especially by exo-cyclically double-bonded oxygen (keto oxygen) and/or by $C_1$–$C_8$alkyl and/or by $C_5$–$C_{10}$-cycloalkyl radicals and/or to contain C=C double bonds;
Z is hydrogen; ammonium; an alkali metal ion; especially lithium, sodium, potassium, ½ equivalent of an alkaline earth metal ion, preferably calcium, magnesium, or the cation of an organic nitrogen base used for neutralisation of the free acid group,
$R_{59}$ and $R_{60}$ are each independently of the other hydrogen, $C_1$–$C_8$alkyl or $C_5$–$C_{10}$cycloalkyl; and
n and m are each independently of the other 0 or 1.
Preferred diphenylmalonic acid nitrites suitable for use according to the invention correspond to formula

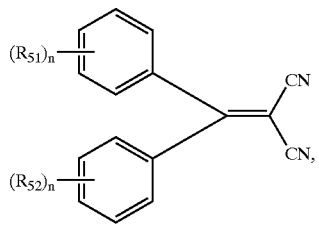 (34)

wherein
$R_{61}$ and $R_{62}$ are each independently of the other $C_1$–$C_{12}$alkyl; or $C_1$–$C_{12}$alkoxy; and
n is 0–3
Further organic UV filters suitable for use according to the invention correspond to formula

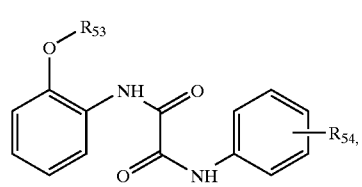 (35)

wherein
$R_{63}$ and $R_{64}$ are each independently of the other $C_1$–$C_5$alkyl, especially ethyl.
Further preferred chemical compound classes of UV filters suitable for use according to the invention are:
p-aminobenzoic acid derivatives (PABA), especially 2-ethylhexyl-4-dimethylamino-benzoate;
salicylic acid derivatives, especially 2-ethylhexyl salicylates; homosalates; and isopropyl salicylates;
benzophenone derivatives, especially benzophenone-2, -3 and -4;

dibenzoylmethane derivatives, especially 1-(4-tert-butylphenyl)-3-(4-methoxyphenyl)-propane-1,3-dione or butylmethoxydibenzoylmethane;

diphenyl acrylates, especially 2-ethylhexyl-2-cyano-3,3-diphenyl acrylate, ethyl 2-cyano-3,3'-diphenyl acrylate and 3-(benzofuranyl)-2-cyanoacrylate;

3-imidazol-4-yl-acrylic acid and 3-imidazol-4-yl acrylate;

benzofuran derivatives, especially the p-aminophenylbenzofuran derivatives disclosed in EP-A-582 189, U.S. Pat. No. 5,338,539 and U.S. Pat. No. 5,518,713;

camphor derivatives, especially 3-(4'-methyl) benzylidenebornan-2-one, 3-benzylidene-bornan-2-one, N-[2(and 4)-2-oxyborn-3-ylidenemethyl)benzyl] acrylamide polymer, 3-(4'-trimethylammonium) benzylidenebornan-2-one methyl sulfate, 3,3'-(1,4-phenylene-dimethine)-bis(7,7-dimethyl-2-oxobicyclo [2.2.1]heptane-1-methanesulfonic acid) and salts thereof, 3-(4'-sulfo)benzylidenebornan-2-one and salts thereof, and also menthyl o-aminobenzoate.

Preferably the following mixtures of organic UV filters are used:

mixtures of methylene bis-benzotriazolyl tetramethylbutylphenol and octyl triazone;

mixtures of octyl triazone and methylene bis-benzotriazolyl tetramethylbutylphenol;

mixtures of 2-[(2,4-methoxy)-phenyl]4,6-bis[(2-hydroxy-4-methoxy)-phenyl]-(1,3,5)-triazine and methylene bis-benzotriazolyl tetramethylbutylphenol;

mixtures of methylene bis-benzotriazolyl tetramethylbutylphenol and dioctyl butamido-triazone;

mixtures of methylene bis-benzotriazolyl tetramethylbutylphenol and octyl-2,2'-methylene bis[6-(2H-benzotriazol-2-yl))-4-methyl-phenol, mixtures of octyl triazone and tris-resorcinyl triazine;

mixtures of 2,2'-methylene bis(6-(2H-benzotriazol-2-yl)-4-methyl-phenol, octyl triazone and the compound of formula (36)

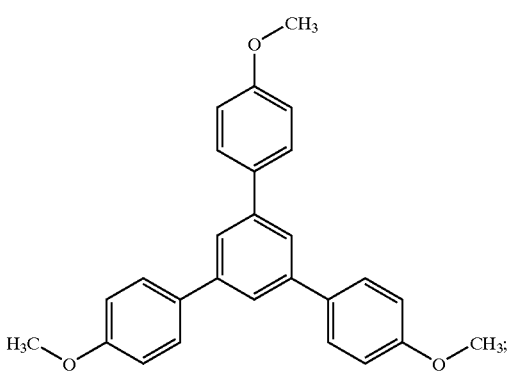

mixtures of 2,2'-methylene bis[6-(2H-benzotriazol-2-yl)-4-methyl-phenyol, octyl triazone and the compound of formula (37)

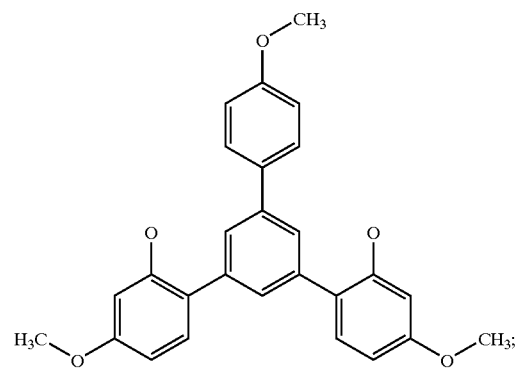

mixtures of methylene bis-benzotriazolyl tetramethylbutylphenol, octyl triazone and the compound of formula (38)

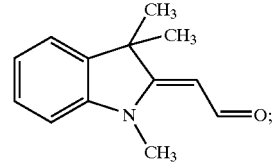

mixtures of methylene bis-benzotriazolyl tetramethylbutylphenol and the compound of (39)

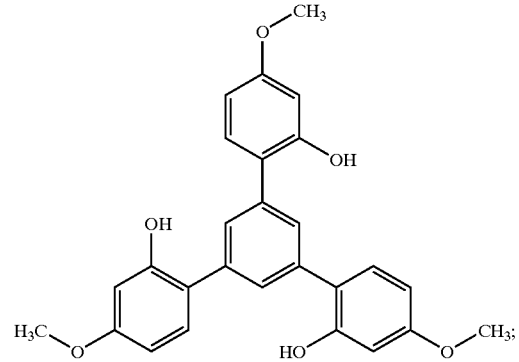

mixtures of methylene bis-benzotriazolyl tetramethylbutylphenol, dioctyl butamido-triazone and the compound of formula (37).

In the radicals defined above, $C_1$–$C_{18}$alkyl denotes straight-chain or branched alkyl radicals, e.g. methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl, hexadecyl, heptadecyl and octadecyl.

$C_1$–$C_{18}$Alkoxy radicals are straight-chain or branched alkyl radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$–$C_{18}$Alkenyl is e.g. allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec4-enyl.

The mixtures of micronised organic UV filters suitable for use according to the invention can be prepared in various ways:

In a first method, at least two of the above-mentioned organic UV filters can be mixed, as single substances, during the process for the preparation of the microparticles (micronisation).

A further possible preparation method comprises intimately mixing together the single substances of the UV filters which have already been micronised.

A third possible preparation method comprises melting together at least two of the UV filters mentioned above. After the melt has cooled, a homogeneous composite is obtained, which is micronised in customary manner.

The invention relates also to the homogeneous composites of at least two organic UV filters.

The invention relates also to composites obtainable by melting one or more inorganic micropigments into one or more organic UV filters.

Examples of micropigments are $TiO_2$, ZnO, iron oxides and other inorganic oxides, mica and other suitable inorganic minerals, and also titanium salts, alkaline earth metal salts and zinc salts of organic acids.

As a result, the undesirable photocatalytic properties of some of those inorganic micro-pigments ($TiO_2$, ZnO) can be suppressed at the same time and their positive properties additionally fully utilised.

Advantageously the above-mentioned inorganic UV filters are melted into methylene bis-benzotriazolyl tetramethylbutylphenol The composite so obtained is then micronised in customary manner.

The invention relates also to composites obtainable by melting at least two electrically neutral organic UV filters with cationically or anionically charged compounds.

For that purpose, cationically or anionically charged compounds are melted with the corresponding organic, electrically neutral UV filters and then cooled. By means of that process it is possible in the subsequent micronisation step to prepare organic UV filter pigments that are permanently provided with a positive or negative charge. Such provision effectively prevents the aggregation of the micronised particles in the sunscreen preparations, which may occur when the particle diameter is <1 μm. Providing the particles with a "coating" having a repellent effect, which is otherwise customary, is then superfluous in some cases.

As cationically or anionically charged compounds it is possible to use UV filters or other compounds having one or more cationic or anionic groupings, e.g.

N,N,N-trimethyl-4-(2-oxoborn-3-ylidenemethyl)-aniline methyl sulfate;
camphor benzalkonium methosulfate;
fatty amines;
betaines, e.g. cocamidopropyl betaine;
quats, e.g. ricinoleamidopropyltrimodium methosulfate, Quaternium 18 or cetyltrimethyl-ammonium bromide;
behenic acid and other organic acids, e.g. isostearic acid, citric acid monoglyceride or sodium methylcocoyl taurate;
phospholipids, e.g. phosphatidylcholine, phosphatidylserine or alkylamine oxide;
ceramides and pseudoceramides and phytosterols.

The last-mlentioned compounds impart oleophobic properties to the micronised UV filters.

The proportion of cationic or anionic compounds in the composite is from 0.001 to 5% by weight, preferably from 0.01 to 3% by weight, based on the weight of the UV filter(s).

The invention relates also to composites obtainable by melting at least one sparingly soluble or insoluble organic UV filter with-antioxidants.

For that purpose, the sparingly soluble or insoluble organic UV filter(s) is/are melted together with antioxidants, cooled and then micronised in customary manner.

Antioxidants suitable for use according to the invention include all organic substances having scavenger properties that can be melted together with organic UV filters. New micro-pigments are obtained that offer simultaneously UV protection and an antioxidative action on their surface. That property is desirable in the case of cosmetic sunscreens, because the influence of UV and light can bring about the formation of damaging free radicals both in formulations and on the skin, which can result, for example, in so-called Mallorca acne or in premature skin ageing. Providing the micronised UV filters with antioxidants, in addition to giving protection against UV damage, simultaneously provides protection against photo-chemical degradation of constituents of the sunscreen formulation.

The proportion of antioxidants in the composite is generally from 0.001 to 30% by weight, preferably from 0.01 to 3% by weight, based on the weight of the UV filter(s).

A content of antioxidants in micropigments is especially advantageous when the latter, comprise, in addition to organic UV filters, also the above-mentioned photocatalytically active inorganic micropigments, e.g. titanium dioxide, zinc oxide (also coated) or other suitable inorganic oxides, e.g. iron oxide.

The following compounds may be mentioned as examples of antioxidants:

tocopherols, e.g. α-tocopherol (CAS 59-02-9), tocopheryl acetate, vitamin E succinate, ellagic acid

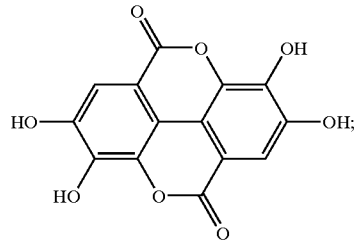

propyl gallate (CAS 121-79-9)

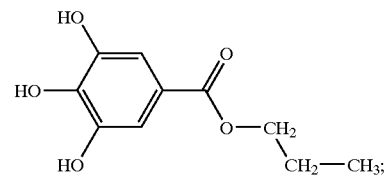

N-butylated hydroxytoluene (BHT; CAS 128-37-0);

butylated hydroxyanisole (BHA);

2,4,6-tris(3,5-di-tert-butyl-4-hydroxybenzyl)mesitylene (CAS 1709-70-2)

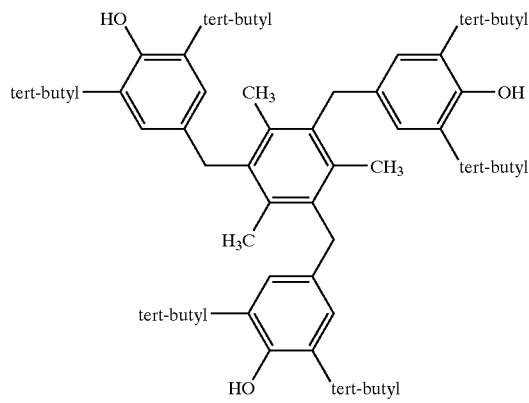

tetrakis[methylene-3-(3',5'-di-tert-butyl-4'-hydroxyphenyl)propionate]methane (CAS 6683-19-8); the compound of formula

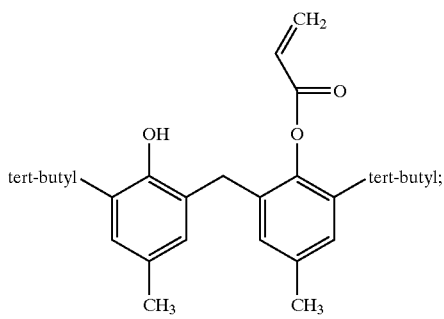

the compound of formula

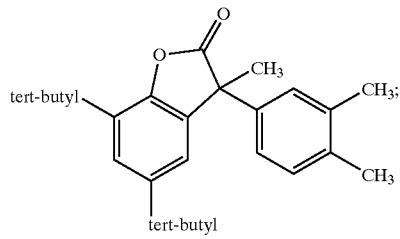

vanillin;
ubiquinone;
ferulic acid and derivatives;
rutinic acid and derivatives;
urocanic acid and derivatives; and
propolis.

Preferably the following mixtures of antioxidants and organic UV filters are used:

mixtures of methylene bis-benzotriazolyl tetramethylbutylphenol, octyl triazone, titanium dioxide and tocopherol, mixtures of 2,2'-methylene bis[6-(2H-benzotriazol-2-yl)-4-methyl-phenol, octyl triazone, tris-resorcinyl triazine and vitamin E mixtures of methylene bis-benzotriazolyl tetramethylbutylphenol, octyl triazone, the compound of formula

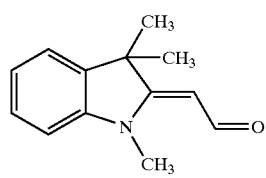

(103)

("Fischer aldehyde") and the compound of formula

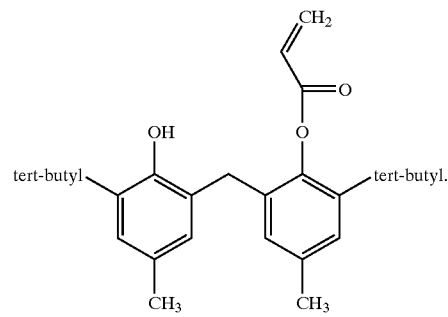

The invention relates also to composites obtainable by melting meltable cosmetic, plant-based and pharmaceutical active ingredients into organic UV filters.

In general it is possible to use micronised UV filters as carriers of highly active substances, especially cosmetic and/or pharmaceutical active ingredients. The advantage of such composites lies in the possibility of releasing the active ingredient(s) from the solids (slow release). Slow release ensures that highly active substances, e.g. anti-inflammatories, cosmetic active ingredients or trace elements, e.g. $Zn^{2+}$ or $Mg^{2+}$, are also uniformly effective over the entire period of use of the UV pigments.

Examples of active ingredients that may be used include:

active ingredients for providing antimicrobial properties and, simultaneously, anti-inflammatory action, e.g triclosan or diclosan;

anti-inflammatory active ingredients, e.g. farnesol, panthenol and avocado oil;

active ingredients having a deodorant or antiperspirant action, e.g. zinc ricinoleates and alkyl citrates;

undecylenic acid and derivatives thereof (e.g. diethanolamides)

zinc undecylate;

pyrithiones, e.g. sodium pyrithione;

odorants or odorant mixtures incorporated by melting, e.g. menthol, geraniol etc., that impart a permanent odour of uniform intensity to such micropigments and to formulations comprising them.

For the preparation of the micropigment mixtures it is possible to use any known processes that are suitable for the preparation of microparticles, e.g.:

wet-grinding with a hard grinding medium, for example zirconium silicate and a protective surfactant or a protective polymer in water or in a suitable organic solvent;

spray-drying from a suitable solvent, for example aqueous suspensions or suspensions containing organic solvents, or true solutions in water, ethanol, dichloroethane, toluene or N-methylpyrrolidone etc..

by the expansion according to the RESS process (Rapid Expansion of Supercritical Solutions) of supercritical fluids (e.g., $CO_2$) in which the UV filter(s) is/are dissolved, or the expansion of fluid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As grinding apparatus for the preparation of the micronised organic UV absorbers according to the invention there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or especially a phospho-lipid.

The micropigments and mixtures of micropigments so obtained generally have an average particle size of from 0.02 to 2 nm, preferably from 0.05 to 1.5 nm and more especially from 0.1 to 1.0 nm.

By virtue of their lipophilicity, they can satisfactorily be incorporated, alone or together with other soluble organic UV absorbers, into oil-containing and fat-containing cosmetic formulations, such as oils, O/W or W/O emulsions, fatty sticks or gels, in accordance with known methods.

Surprisingly, the formulations obtained have the same or better protective action when soluble UV absorbers are used in smaller amounts or even not at all.

The invention relates also to a cosmetic formulation comprising a mixture of micropigments, optionally one or more antioxidants and/or inorganic pigments and/or a cationic or anionic compound, and also cosmetically acceptable carriers or adjuvants.

Cosmetic formulations according to the invention may be contained in a wide variety of cosmetic preparations. Especially the following preparations, for example, come into consideration:

skin-care preparations, e.g. skin-washing and cleansing preparations in the form of tablet-form or liquid soaps, synthetic detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers,nail hardeners or cuticle removers;

intimate hygiene preparations, e.g. intimate washing lotions or intimate sprays;

foot-care preparations, e.g. foot baths, foot powders, foot creams or foot balsams, special deodorants and antiperspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel toothpastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations, e.g. hydrogentperoxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations listed may be in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Advantageously the cosmetic formulations according to the invention may comprise further substances that absorb UV radiation in the UVB range. In that case the total amount of filter substances is from 0.1 to 30% by weight, preferably from 0.5 to 10% by weight, especially from 1 to 6% by weight, based on the total weight of the composition.

As additional UVB filters there come into consideration especially oil-soluble, non-micronised compounds, e.g. organic UV absorbers from the class of the p-aminobenzoic acid derivatives, salicylic acid derivatives, benzophenone derivatives, dibenzoylmethane derivatives, diphenyl acrylate derivatives, benzofuran derivatives, polymeric UV absorbers, comprising one or more organosilicon radicals, cinnamic acid derivatives, camphor derivatives, trianilino-s-triazine derivatives, phenylbenzimidazolesulfonic acid and salts thereof, menthyl anthranilates, benzotriazole derivatives, and/or an inorganic micropigment selected from TiO$_2$, zinc oxide and mica, each encapsulated with aluminium oxide or silicon dioxide.

The following compounds are examples of p-aminobenzoic acid derivatives:
4-aminobenzoic acid (PABA); ethyldihydroxypropyl-PABA of formula

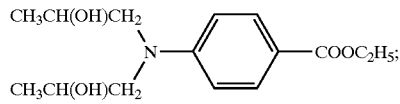

PEG-25-PABA of formula

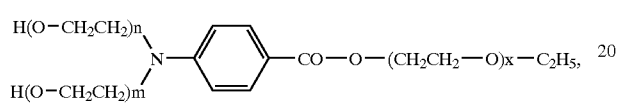

wherein m, n and x have the same meanings and are each a maximum of 25;
octyldimethyl PABA of formula

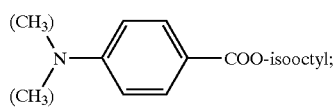

and glycyl amino-benzoate of formula

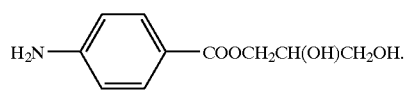

The following compounds are examples of salicylic acid derivatives:
homomenthyl salicylate of formula

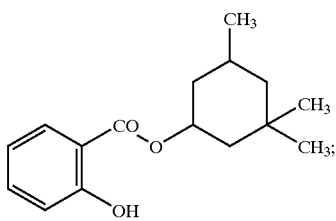

triethanolamine salicylate of formula

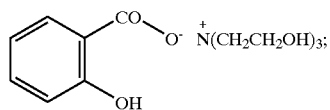

amyl p-dimethylaminobenzoate of formula

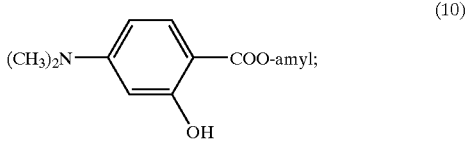

(10)

octyl salicylate of formula

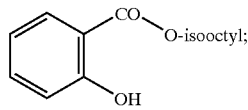

and 4-isopropylbenzyl salicylate of formula

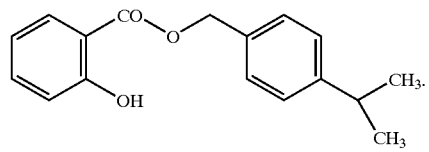

The following compounds are examples of benzophenone derivatives:
benzophenone-3-(2-hydroxy-4-methoxybenzophenone), benzophenone-4-(2-hydroxy-4-methoxybenzophenone-5-sulfonic acid) and benzophenone-8-(2,2'-dihydroxy-4-methoxybenzophenone).

The following compound is an example of a dibenzoylmethane derivative:
butylmethoxydibenzoylmethane-[1-(4-tert-butyl)-3-(4-methoxyphenyl)propane-1,3-dione].

The following compounds are examples of diphenyl acrylate derivatives:
octocrylene (2-ethylhexyl-2-cyano-3,3'-diphenyl acrylate) and etocrylene (ethyl-2-cyano-3,3'-diphenyl acrylate).

The following compounds are examples of benzofuran derivatives:
3-(benzofuranyl)-2-cyanoacrylate, 2-(2-benzofuranyl)-5-tert-butylbenzoxazole and 2-(p-aminophenyl)benzofuran and especially the compound of formula

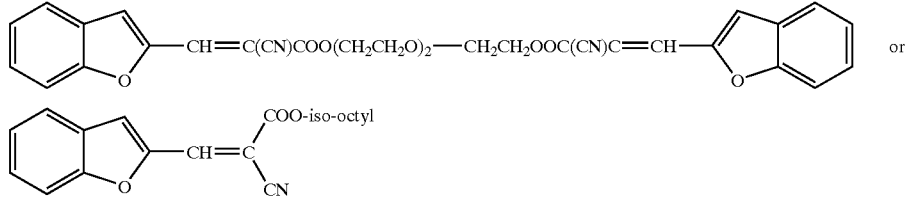 or

The following compounds are examples of polymeric UV absorbers that contain one or more organosilicon radicals: a benzylidene malonate derivative, especially the compound of formula

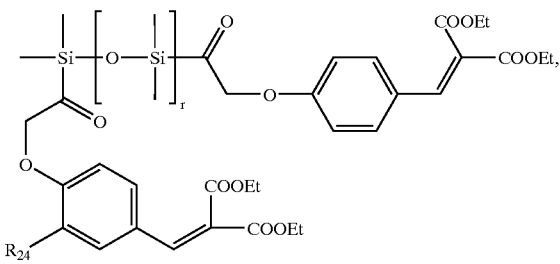

wherein
$R_{24}$ is hydrogen or methoxy and
r is approximately 7; the compound of formula

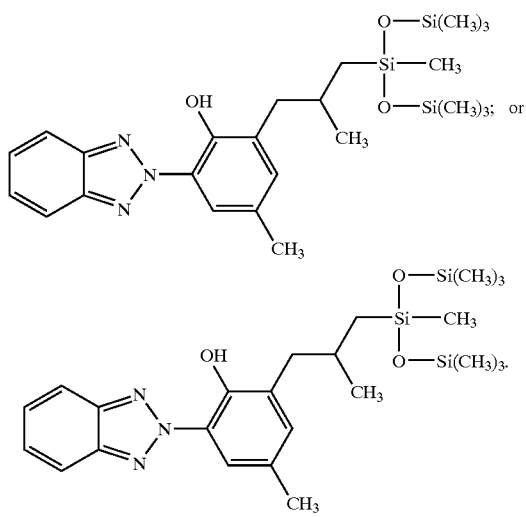

The following compounds are examples of cinnamic acid esters:
octyl methoxycinnamate (4-methoxycinnamic acid 2-ethylhexyl ester), diethanolamine methoxycinnamate (diethanolamine salt of 4-methoxycinnamic acid), isoamyl p-methoxycinnamate (4-ethoxycinnamic acid 2-isoamyl ester), 2,5-diisopropylmethyl cinnamate and a cinnamic acid amido derivative.

The following compounds are examples of camphor derivatives:
4-methyl-benzylidene camphor [3-(4'-methyl)benzylidene-bornan-2-one], 3-benzylidene camphor (3-benzylidene-bornan-2-one), polyacrylamidomethylbenzylidene camphor {N-[2(and 4)-2-oxyborn-3-ylidene-methyl)benzyl] acrylamide polymer}, trimonium-benzylidene camphor sulfate [3-(4'-trimethylammonium)-benzylidene-bornan-2-one methyl sulfate], terephthalydene dicamphorsulfonic acid {3,3'-(1,4-phenylenedimethine)-bis(7,7-dimethyl-2-oxo-bicyclo[2.2.1]heptane-1-methanesulfonic acid} or salts thereof, and benzylidene camphorsulfonic acid [3-(4'-sulfo)benzylidene-bornan-2-one] or salts thereof.

The following compounds are examples of trianilino-s-triazine derivatives:
octyl triazine-[2,4,6-trianilino-(p-carbo-2'-ethyl-1'-oxy)-1,3,5-triazine, and the trianilino-s-triazine derivatives described in U.S. Pat. Nos. 5,332,568, 5,252,323, WO 93/17002 and WO 97/03642 and EP-A-0 517 104.

The following compound is an example of a benzotriazole:
2-(2-hydroxy-5-methyl-phenyl)benzotriazole.

The following Examples serve to illustrate the invention but do not limit the invention thereto. The cosmetic active substances are primarily given with their INCI name (INCI= International Norm of Cosmetical Ingredients).

EXAMPLE 1

50 parts of methylene bis-benzotriazolyl tetramethylbutylphenol and 50 parts of octyl triazone are ground together with a grinding medium of zirconium silicate sand, a protective surfactant (alkyl polyglucoside) and water in a bead mill to form a mixed micropigment having a $d_{50}$ of 190 nm. When the grinding medium has been separated off, the suspension of the mixed micropigment can be used in the preparation of sunscreen formulations.

EXAMPLE 2

32 parts of octyl triazone, 1 part of cetyltrimethylammonium bromide and 66 parts of methylene bis-benzotriazolyl tetramethylbutylphenol are melted together homogeneously. The melt is rapidly cooled to room temperature and the solidified melt is comminuted mechanically (hammer mill). The powder so obtained is suspended in water; decyl glycoside is, added and the mixture is micronised together with a grinding aid ('heavy sand') to a particle size of $d_{50}$ 200 nm diameter. When the grinding aid has been separated off, an aqueous suspension of the micronised UV absorber composite is obtained. The suspension is rendered slightly acidic with citric acid and can be used in the preparation of cosmetic and pharmaceutical formulations.

EXAMPLE 3

25 parts of 2-[(2,4-methoxy)-phenyl]-4,6-bis[(2-hydroxy-4-methoxy)-phenyl]-(1,3,5)-triazine, 74 parts of methylene bis-benzotriazolyl tetramethylbutylphenol and 1 part of tetrakis-[methylene-3-(3',5'-di-tert-butyl-4'-hydroxyphenyl) propionate]methane are melted together homogeneously. The melt is rapidly cooled to room temperature and the solidified melt is comminuted mechanically (hammer mill). The powder so obtained is suspended in water; first decyl glyciside and then, after further grinding, ceteareth-25 are added and the mixture is micronised together with a grinding aid ('heavy sand') to a particle size of $d_{50}$ 190 nm diameter. When the grinding aid has been separated off, an aqueous suspension of the micronised UV absorber composite is obtained which can be used in the preparation of cosmetic and pharmaceutical formulations.

EXAMPLE 4

25 parts of dioctyl butamidotriazone are dissolved in 75 parts of molten methylene bis-benzotriazolyl tetramethylbutylphenol. The mixture is cooled rapidly, comminuted mechanically to form a fine powder and then ground with a grinding medium of zirconium silicate sand, a protective surfactant (phospholipid) and water to form a micropigment of $d_{50}$ 300 nm. The suspension of the micropigment is separated from the grinding medium and used in the preparation of sunscreen formulations.

EXAMPLE 5

24 parts of octyl triazone, 5 parts of titanium dioxide and one part of tocopherol are mixed into 70 parts of molten methylene bis-benzotriazolyl tetramethylbutylphenol. The mixture is cooled rapidly, comminuted mechanically to form a fine powder and then ground with a grinding medium of zirconium silicate sand, a protective surfactant (alkyl polyglucoside) and water to form a micropigment. The suspension of the micropigment is separated from the grinding medium and used in the preparation of sunscreen formulations.

In the following Examples 6 to 11, suspensions of microcomposites of the following compositions are prepared analogously to Examples 1 and 2:

EXAMPLE 6

60 parts of 2,2'-methylene bis[6-(2H-benzotriazol-2-yl)-4-methyl-phenol, 20 parts of octyl triazone, 19 parts of tris-resorcinyl triazine and 1 part of vitamin E, adjusted to pH 6.5 with citric acid.

EXAMPLE 7

60 parts of 2,2'-methylene bis[6-(2H-benzotriazol-2-yl)-4-methyl-phenol, 20 parts of octyl triazone and 20 parts of the compound of formula (101)

EXAMPLE 8

59 parts of 2,2'-methylene bis[6-(2H-benzotriazol-2-yl)-4-methyl-phenol, 20 parts of octyl triazone, 20 parts of the compound of formula

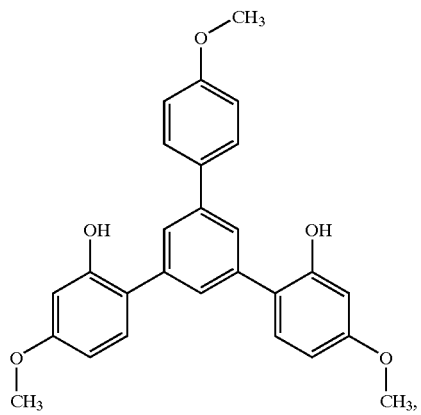

(102)

adjusted to pH 6.5 with citric acid.

EXAMPLE 9

75 parts of methylene bis-benzotriazolyl tetramethylbutylphenol, 10 parts of octyl triazone (grinding at pH<5, adjusted with citric acid), 14 parts of the compound of formula (103)

("Fischer aldehyde") and 1 part of the compound of formula

EXAMPLE 10

80 parts of methylene bis-benzotriazolyl tetramethylbutylphenol, and 20 parts of the compound of formula

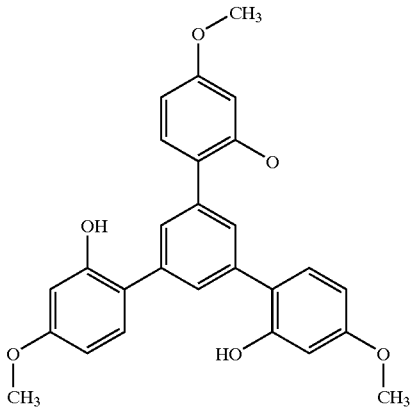
(104)

EXAMPLE 11

50 parts of methylene bis-benzotriazolyl tetramethylbutylphenol, 10 parts of dioctyl butamidotriazone (grinding at pH<5, adjusted to pH 6.5 with citric acid) and 20 parts of the compound of formula (102).

| | | % |
|---|---|---|
| Example 12: O/W Sunscreen lotion | | |
| A | Polyglyceryl-3 methylglucose distearate | 2.0 |
| | Decyl oleate | 5.7 |
| | isopropyl palmitate | 6.0 |
| | Caprylic/capric triglyceride | 7.5 |
| B | Glycerol | 3.0 |
| | Phenonip | 0.5 |
| | Water | 69.3 |
| C | Carbomer | 0.2 |
| | Isopropyl palmitate | 0.8 |
| D | Micropigment from Example 2 | 5.0 |
| E | NaOH (10%) | as required |
| Example 13: O/W Emulsion | | |
| | Potassium cetyl phosphate | 2.00 |
| | Tricontanyl PVP | 1.00 |
| | Caprylic/capric triglyceride | 5.00 |
| | Cetearyl isononanoate | 5.00 |
| | $C_{12-15}$ Alkyl benzoate | 5.00 |
| | Glyceryl stearate | 3.00 |
| | Cetyl alcohol | 1.00 |
| | Phenoxyethanol & parabens | 1.00 |
| | Octyl methoxycinnamate | 5.00 |
| | Dimethicone | 0.10 |
| | Deionised water | 64.15 |
| | Carbomer (Carbopol 981) | 0.10 |
| | Glycerol | 3.00 |
| | NaOH (10%) | 1.00 |
| | Micropigment from Example 1 | 4.00 |
| Example 14: O/W Emulsion: | | |
| | Cetearyl alcohol & dicetyl phosphate & ceteth-10 phosphate | 6.00 |
| | Caprylic/capric triglyceride | 5.00 |
| | Cetearyl isononanoate | 5.00 |
| | $C_{12-15}$ Alkyl benzoate | 5.00 |
| | Phenoxyethanol & parabens | 1.00 |
| | Octyl methoxycinnamate | 5.00 |
| | Dimethicone | 0.20 |
| | Deionised water | 64.70 |
| | Carbomer (Carbopol 981) | 0.10 |
| | Glycerol | 3.00 |
| | NaOH (10%) | 0.65 |
| | Micropigment from Example 3 | 4.00 |
| Example 15: O/W Emulsion: | | |
| | Isopropyl myristate & trilaureth-4 phosphate | 5.00 |
| | Tricontanyl PVP | 1.00 |
| | Caprylic/capric triglyceride | 5.00 |
| | Cetearyl isononanoate | 2.00 |
| | $C_{12-15}$ Alkyl benzoate | 5.00 |
| | Glyceryl stearate | 2.00 |
| | Cetyl alcohol | 1.00 |
| | Phenoxyethanol & parabens | 1.00 |
| | Octyl methoxycinnamate | 5.00 |
| | Dimethicone | 0.10 |
| | Deionised water | 66.30 |
| | Carbomer (Carbopol 981) | 0.10 |
| | Glycerol | 3.00 |
| | NaOH (10%) | 0.50 |
| | Micropigment from Example 4 | 4.00 |
| Example 16: O/W Emulsion | | |
| | Sodium stearyl lactate tricontanyl PVP | 1.50 |
| | Tricontanyl PVP | 1.00 |
| | Caprylic/capric triglyceride | 5.00 |
| | Cetearyl isononanoate | 5.00 |
| | $C_{12-15}$ Alkyl benzoate | 5.00 |
| | Glyceryl stearate | 3.50 |
| | Cetyl alcohol | 2.00 |
| | Phenoxyethanol & parabens | 1.00 |
| | Octyl methoxycinnamate | 5.00 |
| | Dimethicone | 0.20 |
| | Deionised water | 63.60 |
| | Carbomer (Carbopol 981) | 0.10 |
| | Glycerol | 3.00 |
| | NaOH (10%) | 0.10 |
| | Micropigment from Example 6 | 4.00 |
| Example 17: O/W Emulsion | | |
| | Cetearyl alcohol & sodium cetearyl sulfate | 5.00 |
| | Caprylic/capric triglyceride | 5.00 |
| | Cetearyl isononanoate | 5.00 |
| | $C_{12-15}$ Alkyl benzoate | 5.00 |
| | Phenoxyethanol & parabens | 1.00 |
| | Octyl methoxycinnamate | 5.00 |
| | Dimethicone | 0.10 |
| | Deionised water | 65.90 |
| | Glycerol | 3.00 |
| | NaOH (10%) | 0.30 |
| | Micropigment from Example 9 | 4.00 |
| Example 18 : O/W Emulsion | | |
| | Lauryl glucoside & polyglyceryl-2 dihydroxystearate & glycerol | 3.00 |
| | Tricontanyl PVP | 1.00 |
| | Caprylic/capric triglyceride | 4.00 |
| | Cetearyl isononanoate | 4.00 |
| | $C_{12-15}$ Alkyl benzoate | 5.00 |
| | Glyceryl stearate | 2.00 |
| | Cetyl alcohol | 3.00 |
| | Phenoxyethanol & parabens | 1.00 |
| | Octyl methoxycinnamate | 5.00 |
| | Dimethicone | 0.20 |
| | Deionised water | 64.49 |
| | Carbomer (Carbopol 981) | 0.10 |
| | Glycerol | 3.00 |
| | NaOH (10%) | 0.21 |
| | Micropigment from Example 8 | 4.00 |
| Example 19: O/W Emulsion: | | |
| | Cetaryl glucoside & cetearyl alcohol | 4.50 |
| | Tricontanyl PVP | 1.00 |
| | Caprylic/capric triglyceride | 5.00 |
| | Cetearyl isononanoate | 5.00 |
| | $C_{12-15}$ Alkyl benzoate | 5.00 |
| | Phenoxyethanol & parabens | 1.00 |
| | Octyl triazone | 3.00 |

|  | % |
|---|---|
| 4-Methylbenzylidene camphor | 3.00 |
| Dimethicone | 0.20 |
| Deionised water | 64.65 |
| Steareth-10 allyl ether(acrylates copolymer | 5.00 |
| Glycerol | 3.00 |
| NaOH (10%) | 1.00 |
| Micropigment from Example 2 | 4.00 |

Example 20: O/W Emulsion

|  | % |
|---|---|
| Cetearyl glucoside | 5.00 |
| Tricontanyl PVP | 1.00 |
| Caprylic/capric triglyceride | 5.00 |
| Cetearyl isononanoate | 5.00 |
| $C_{12-15}$ Alkyl benzoate | 5.00 |
| Phenoxyethanol & parabens | 1.00 |
| Octocrylene | 3.00 |
| Octyl methoxycinnamate | 4.00 |
| Dimethicone | 0.20 |
| Deionised water | 63.15 |
| Carbomer (Carbopol 981) | 0.50 |
| Glycerol | 3.00 |
| NaOH (10%) | 0.15 |
| Micropigment from Example 2 | 4.00 |

Example 21: O/W Emulsion:

|  | % |
|---|---|
| Polyglyceryl-10 petasterate & behenyl alcohol & sodium stearoyl laurate | 2.50 |
| Caprylic/capric triglyceride | 5.00 |
| Cetearyl isononanoate | 5.00 |
| $C_{12-15}$ Alkyl benzoate | 5.00 |
| Glyceryl stearate | 3.00 |
| Cetearyl alcohol | 2.00 |
| Phenoxyethanol & parabens | 1.00 |
| Octyl methoxycinnamate | 5.00 |
| Dimethicone | 0.20 |
| Deionised water | 64.75 |
| Carbomer (Carbopol 981) | 0.15 |
| Glycerol | 3.00 |
| NaOH (10%) | 0.40 |
| Micropigment from Example 9 | 4.00 |

Example 22: O/W Emulsion:

|  | % |
|---|---|
| Palmitic acid & stearic acid | 1.80 |
| Glyceryl stearate SE | 3.00 |
| Tricontanyl PVP | 1.00 |
| Caprylic/capric triglyceride | 5.00 |
| Cetearyl isononanoate | 5.00 |
| $C_{12-15}$ Alkyl benzoate | 5.00 |
| Glyceryl stearate | 0.50 |
| Phenoxyethanol & parabens | 1.00 |
| Octyl dimethyl PABA | 5.00 |
| Dimethicone | 0.10 |
| Deionised water | 64.15 |
| Carbomer (Carbopol 981) | 0.10 |
| Glycerol | 3.00 |
| NaOH (10%) | 0.50 |
| Micropigment from Example 1 | 4.00 |

Example 23: O/W Emulsion:

|  | % |
|---|---|
| Glyceryl stearate & PEG 100 stearate | 3.00 |
| Tricontanyl PVP | 1.00 |
| Caprylic/capric triglyceride | 5.00 |
| Cetearyl isononanoate | 5.00 |
| $C_{12-15}$ Alkyl benzoate | 5.00 |
| Cetearyl alcohol | 3.00 |
| Phenoxyethanol & parabens | 1.00 |
| Octyl methoxycinnamate | 5.00 |
| Dimethicone | 0.10 |
| Deionised water | 64.60 |
| Carbomer (Carbopol 981) | 0.10 |
| Glycerol | 3.00 |
| NaOH (10%) | 0.20 |
| Micropigment from Example 3 | 4.00 |

Example 24: O/W Emulsion:

|  | % |
|---|---|
| Steareth-2 | 2.50 |
| Steareth-21 | 1.00 |
| Tricontanyl PVP | 1.00 |
| Caprylic/capric triglyceride | 5.00 |
| Cetearyl isononanoate | 5.00 |
| $C_{12-15}$ Alkyl benzoate | 5.00 |
| Cetyl alcohol | 1.00 |
| Phenoxyethanol & parabens | 1.00 |
| Methyl anthranilate | 3.00 |
| Octyl methoxycinnamate | 4.00 |
| Dimethicone | 0.10 |
| Deionised water | 63.95 |
| Carbomer (Carbopol 981) | 0.20 |
| Glycerol | 3.00 |
| NaOH (10%) | 0.25 |
| Micropigment from Example 4 | 4.00 |

Example 25: O/W Emulsion:

|  | % |
|---|---|
| Glyceryl stearate & cetareth-20 & cetareth-12 & cetaryl alcohol & cetyl palmitate | 5.00 |
| Tricontanyl PVP | 1.00 |
| Caprylic/capric triglyceride | 5.00 |
| Cetearyl isononanoate | 5.00 |
| $C_{12-15}$ Alkyl benzoate | 5.00 |
| Phenoxyethanol & parabens | 1.00 |
| 4-methylbenzylidene camphor | 5.00 |
| Dimethicone | 0.10 |
| Deionised water | 65.60 |
| Carbomer (Carbopol 981) | 0.10 |
| Glycerol | 3.00 |
| NaOH (10%) | 0.20 |
| Micropigment from Example 3 | 4.00 |

Example 26: O/W Emulsion

|  | % |
|---|---|
| Octyldecyl phosphate | 3.00 |
| Tricontanyl PVP | 1.00 |
| Caprylic/capric triglyceride | 5.00 |
| Cetearyl isononanoate | 5.00 |
| $C_{12-15}$ Alkyl benzoate | 5.00 |
| Phenoxyethanol & parabens | 1.00 |
| Octyl methoxycinnamate | 5.00 |
| Dimethicone | 0.10 |
| Deionised water | 64.50 |
| Sodium cocoyl glutamate | 0.60 |
| Steareth-10 allyl ether/acrylates copolymer | 0.50 |
| Glycerol | 3.00 |
| NaOH (10%) | 2.30 |
| Micropigment from Example 4 | 4.00 |

Example 27: O/W Emulsion:

|  | % |
|---|---|
| Polyglyceryl-3 methyl glucose distearate | 2.00 |
| Tricontanyl PVP | 1.00 |
| Tocopherol & ascorbyl palmitate & ascorbic acid & citric acid & PEG-8 | 0.05 |
| Decyl oleate | 4.50 |
| Isopropyl palmitate | 6.00 |
| Caprylic/capric triglyceride | 5.00 |
| Glyceryl stearate | 1.00 |
| Cetearyl alcohol | 1.00 |
| 2-[(2,4-Methoxy)-phenyl]-4,6-bis[(2-hydroxy-4-methoxy)-phenyl]-(1,3,5)-triazine | 2.00 |
| Octyl methoxycinnamate | 3.00 |
| Deionised water | 63.12 |
| Phenoxyethanol & parabens | 0.80 |
| Propylene glycol | 3.00 |
| Carbomer (Carbopol 981) | 0.20 |
| NaOH (10%) | 0.33 |
| Scleroglucan | 1.00 |
| Micropigment from Example 2 | 3.00 |
| Titanium dioxide | 3.00 |

Example 28: O/W Emulsion

|  | % |
|---|---|
| Methyl glucose sesquistearate | 2.50 |
| Tricontanyl PVP | 1.00 |
| Tocopherol & ascorbyl palmitate & ascorbic acid & citric acid & PEG-8 | 0.05 |
| Decyl oleate | 4.00 |
| isopropyl palmitate | 6.00 |
| Caprylic/capric triglyceride | 5.00 |

|  | % |
|---|---|
| Glyceryl stearate | 1.00 |
| Cetearyl alcohol | 1.00 |
| 2-[(2,4-Methoxy)-phenyl]4,6-bis[(2-hydroxy-4-methoxy)phenyl]-(1,3,5)-triazine | 2.00 |
| Octyl methoxycinnamate | 5.00 |
| Deionised water | 63.12 |
| Phenoxyethanol & parabens | 0.80 |
| Carbomer (Carbopol 981) | 0.20 |
| Glycerol | 3.00 |
| NaOH (10%) | 0.33 |
| Scleroglucan | 1.00 |
| Micropigment from Example 1 | 4.00 |

Example 29: Lip-care preparation

| Glycerol | 10.00 |
|---|---|
| PEG-45 & dodecyl glycerol copolymer | 1.50 |
| Quaternium-18 bentonite | 2.00 |
| Microcrystalline wax | 2.00 |
| Beeswax | 2.00 |
| Glyceryl stearate SE | 53.00 |
| Pentaerythritil stearate & caprate & caprylate adipate | 4.00 |
| Castor oil | 4.00 |
| Methylene bis-benzotriazolyl tetramethylbutylphenol | 5.00 |
| Micropigment Example 2 | 5.00 |
| Titanium dioxide | 5.00 |
| Zinc oxide | 5.00 |
| Octyl methoxycinnamate | 4.00 |
| Eucerinum anhydricum | ad 100 |

Example 30: W/O Emulsion

| PEG-30 dipolyhydroxystearate | 2.00 |
|---|---|
| Isostearyl alcohol | 20.00 |
| Isostearic acid | 10.00 |
| Octyl triazone | 3.00 |
| Deionised water | 58.75 |
| Glycerol | 5.00 |
| Methylparaben | 0.17 |
| Propylparaben | 0.03 |
| MgSO$_4$ × 7 H$_2$O | 0.75 |
| Micropigment from Example 2 | 4.00 |

Example 31: O/W Emulsion

| A | Polyglyceryl-3 methylglucose distearate | 2.0 |
|---|---|---|
|  | Decyl oleate | 5.7 |
|  | Isopropyl palmitate | 5.0 |
|  | Caprylic/capric triglyceride | 6.5 |
|  | Octyl methoxycinnamate | 5.0 |
| B | Glycerol | 3.0 |
|  | Phenonip | 0.5 |
|  | Deion. water | 62.9 |
| C | Carbomer 141 | 0.2 |
|  | Isopropyl palmitate | 0.8 |
| D | 50% Suspension from Example 8 | 8.0 |
| E | NaOH (10%) | as required |

Example 32: O/W Emulsion

| A | Polyglyceryl-3 methylglucose distearate | 2.0 |
|---|---|---|
|  | Decyl oleate | 5.7 |
|  | Isopropyl palmitate | 5.0 |
|  | Caprylic/capric triglyceride | 6.5 |
| B | Glycerol | 3.0 |
|  | Phenonip | 0.5 |
|  | Deion. water | 62.9 |
| C | Carbomer 141 | 0.2 |
|  | Isopropy palmitate | 0.8 |
| D | Suspension from Example 2 | 6.0 |
| E | NaOH (10%) | as required |

Example 33: (O/W Emulsion)

| A | Polyglyceryl-3 methylglucose distearate | 2.0 |
|---|---|---|
|  | Decyl oleate | 5.7 |
|  | Isopropyl palmitate | 5.0 |
|  | Caprylic/capric triglyceride | 6.5 |
|  | Octyl triazone | 2.0 |
| B | Glycerol | 3.0 |
|  | Phenonip | 0.5 |
|  | Water | 62.3 |
| C | Carbomer 141 | 0.2 |
|  | Isopropyl Palmitate | 0.8 |
| D | 2,2'-Methylene bis(6-(2H-berzotriazol-2-yl)-4-(1,1,3,3-tetramethytbutyl)phenol micropigment suspension (50%) | 8.0 |
|  | Octyl triazone micropigment suspension (50%) | 4.0 |
| E | NaOH (10%) | as required |

Example 34: O/W Emulsion

| A | Polyglyceryl-3 methylglucose distearate | 2.0 |
|---|---|---|
|  | Decyl oleate | 5.7 |
|  | Isopropyl palmitate | 5.0 |
|  | Octyl triazone | 2.0 |
|  | Caprylic/capric triglyceride | 6.5 |
| B | Glycerol | 3.0 |
|  | Phenonip | 0.5 |
|  | Water | 68.3 |
| C | Carbomer 141 | 0.2 |
|  | Isopropyl palmitate | 0.8 |
| D | Micropigment from Example 2 | 6.0 |
| E | NaOH (10%) | as required |

Example 35: W/O Emulsion

| PEG-30 dipolyhydroxystearate (Ariacel P 135 ®) | 3.00 |
|---|---|
| PEG-22/dodecyl glycol copolymer (Elfacos ST 37 ®) | 1.00 |
| Microcrystalline wax | 1.00 |
| Hydrogenated castor oil | 0.50 |
| Magnesium stearate | 1.00 |
| Octyl stearate | 15.00 |
| Coco glycerides | 2.00 |
| Mineral oil | 3.00 |
| Phenoxyethanol & parabens | 1.00 |
| Octyl methoxycinnamate | 5.00 |
| Dimethicone | 0.10 |
| Water | 54.40 |
| Magnesium sulfate (MgSO$_4$ × 7 H$_2$O) | 1.00 |
| Propylene glycol | 4.00 |
| 50% Suspension from Example 3 | 8.00 |

Example 36: W/O Emulsion

| Methoxy PEG-22/dodecyl glycol copolymer (Elfacos E 200 ®) | 3.00 |
|---|---|
| PEG-22/dodecyl glycol copolymer (Elfacos ST 37 ®) | 3.00 |
| Hydroxyoctacosanyl hydroxystearate (Elfacos C 26 ®) | 3.00 |
| Octyl stearate | 15.00 |
| Coco glycerides | 2.00 |
| Mineral oil | 3.00 |
| Phenoxyethanol & parabens | 1.00 |
| 4-Methylbenzylidene camphor | 3.00 |
| Dioctyl butamidotriazone | 3.00 |
| Dimethicone | 0.20 |
| Water | 53.00 |
| Phenylbenzimidazole sulfonic acid | 3.00 |
| Magnesium sulfate (MgSO$_4$ × 7 H$_2$O) | 0.80 |
| Propylene glycol | 4.00 |
| Micropigment from Example 5 | 3.00 |

Example 37: W/O Emulsion

| Polyglyceryl-2 dipolyhydroxystearate (Dehymuls PGPH ®) | 2.00 |
|---|---|
| PEG-30 dipolyhydroxystearate (Arlacel P 135 ®) | 2.00 |
| Hydroxyoctacosanyl hydroxystearate (Elfacos C 26 ®) | 2.00 |
| Zinc stearate | 1.00 |
| Octyl stearate | 15.00 |
| Coco glycerides | 2.00 |
| Mineral oil | 3.00 |
| Phenoxyethanol & parabens | 1.00 |
| 2,4-Bis{[4-(2-ethyl-hexyloxy)-2-hydroxy]-phenyl}-6-(4-methoxy-phenyl)1,3,5)-triazine | 2.00 |
| Octyl salicylate | 3.00 |
| Dimethicone | 0.20 |
| Water | 56.70 |
| Magnesium sulfate (MgSO$_4$ × 7 H$_2$O) | 1.00 |
| Propylene glycol | 4.00 |
| Micropigment from Example 6 | 5.00 |

| | % |
|---|---|
| Example 38: W/O Emulsion | |
| Polyglyceryl-2-dipolyhydroxystearate (Dehymuls PGPH ®) | 3.00 |
| Glyceryl oleate (Monomuls 90-O 18 ®) | 1.00 |
| Caprylic/capric triglyceride | 6.00 |
| Octyldodecanol | 6.00 |
| Cetearyl isononanoate | 5.00 |
| Tocopheryl acetate | 1.00 |
| Cera alba | 1.20 |
| Glycerol (86%) | 5.00 |
| Phenonip | 0.50 |
| Octyl methoxycinnamate | 4.00 |
| Octyl triazone | 3.00 |
| Micropigment from Example 3 | 5.00 |
| Water | ad 100 |
| Example 39: W/O Emulsion | |
| Polyglyceryl-2-dipolyhydroxystearate (Dehymuls PGPH ®) | 3.00 |
| Glyceryl oleate (Monomuls 90-O 18 ®) | 1.00 |
| Caprylic/capric triglyceride | 6.00 |
| Octyldodecanol | 6.00 |
| Cetearyl isononanoate | 5.00 |
| Octyl methoxycinnamate | 3.00 |
| Tocopheryl acetate | 1.00 |
| Cera alba | 1.20 |
| Glycerol (86%) | 5.00 |
| Phenonip | 0.50 |
| Micropigment from Example 10 | 5.00 |
| Water | ad 100 |
| Example 40: O/W Emulsion | |
| Tego Care CG 90 (Goldschmidt AG) | 6.00 |
| Cetearyl alcohol | 1.50 |
| Glyceryl stearate | 0.50 |
| Octyldecanol | 7.00 |
| Capric/caprylic triglyceride | 5.00 |
| Cetearyl isononanoate | 6.00 |
| Octyl methoxycinnamate | 3.00 |
| Deionised water | 51.14 |
| Carbomer | 0.20 |
| NaOH (45%) | 1.13 |
| Glycerol | 5.00 |
| Methylparaben | 0.17 |
| Propylparaben | 0.03 |
| Terephthalydene-dibornanesulfonic acid | 1.50 |
| Micropigment from Example 5 (50% suspension) | 12.00 |
| Example 41: O/W Microemulsion | |
| Ceteareth-12 | 8.0 |
| Cetearyl alcohol | 4.0 |
| Cetearyl isononanoate | 20.0 |
| Butyl methoxydibenzoylmethane | 2.0 |
| Deionised water | ad 100.0 |
| Carbomer | 0.2 |
| Preservative | as required |
| Magnesium sulfate (MgSO₄ × 7 H₂O) | 3.0 |
| Micropigment from Example 9 (50% suspension) | 8.0 |
| Example 42: O/W/O Emulsion | |
| Polyglyceryl-2-polyhydroxystearate | 5.0 |
| Mineral oil | 12.5 |
| Stearic acid | 2.0 |
| Cetearyl isononanoate | 12.5 |
| Methylbenzylidene camphor | 2.0 |
| Homosalate | 2.0 |
| Deionised water | ad 100.0 |
| Carbomer | 0.2 |
| Preservative | as required |
| NaOH | as required |
| Micropigment from Example 2 (50% suspension) | 8.0 |
| Example 43: O/W Emulsion | |
| Glycerol stearate/polyethylene glycol (MW100) stearate | 3.0 |
| Cetyl/stearyl alcohol-20EO (Eumulgin B 2) | 1.0 |
| Cetyl/stearyl alcohol (Lanette O) | 2.0 |
| Caprylic/capric triglyceride (Myritol 318) | 4.0 |
| Dicaprylic ether | 6.0 |
| Mineral oil and Quaternium-18 hectorite | 3.0 |
| Glycerol stearate, cetyl/stearyl alcohol, cetyl palmitate, coco glyceride (Cutina CBS) | 2.0 |
| 4-Methylbenzylidene camphor | 1.0 |
| Octyl triazone | 2.0 |
| Deionised water | ad 100.0 |
| Glycerol, 85% | 3.0 |
| Preservative | as required |
| Magnesium aluminium silicate (Vegum Ultra) | 0.3 |
| NaOH | as required |
| Micropigment from Example 2 (50% suspension) | 10.0 |

What is claimed is:

1. A method of protecting human and animal skin and hair against the damaging effects of UV radiation by treating the skin or hair with a cosmetic formulation, comprising a mixture of micronised organic UV filters selected from the group consisting of: triazine derivatives, benzotriazole derivatives, amides containing a vinyl group, cinnamic acid derivatives, sulfonated benzimidazoles, Fischer base derivatives, diphenylmalonic acid dinitriles, oxalyl amides, camphor derivatives, diphenyl acrylates, para-aminobenzoic acid (PABA) and derivatives thereof, salicylates and benzophenones, wherein the size of the micronized particles is from 0.02 to 2 µm.

2. A method according to claim 1, wherein the organic UV filters are chosen from triazine derivatives of formula

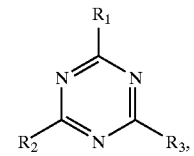

(1)

wherein $R_1$, $R_2$ and $R_3$ are each independently of the others hydrogen; OH; $C_1$–$C_{18}$alkoxy; —$NH_2$; —NH—$R_4$; —N($R_4$)$_2$; or —$OR_4$, $R_4$ is $C_1$–$C_5$alkyl; phenyl; phenoxy; anilino; pyrrolo, wherein phenyl, phenoxy, anilino and pyrrolo are unsubstituted or may be substituted by one, two or three OH groups, carboxy, —CO—$NH_2$, $C_1$–$C_5$alkyl or $C_1$–$C_5$alkoxy; a methylidene-camphor group; a group of formula —(CH=CH)$_m$C(=O)—$OR_4$; a group of formula

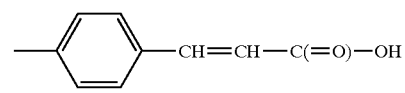

or a corresponding alkali metal, ammonium, mono-, di- or tri-$C_1$–$C_4$alkylammonium, mono-, di- or tri- $C_2$–$C_4$alkanolammonium salt, or a $C_1$–$C_3$alkyl ester thereof; or a radical of formula

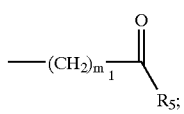
(1a)

$R_5$ is hydrogen; $C_1$–$C_5$alkyl which is unsubstituted or substituted by one or more OH groups; $C_1$–$C_5$alkoxy; amino; mono- or di-$C_1$–$C_5$alkylamino; M; a radical of formula

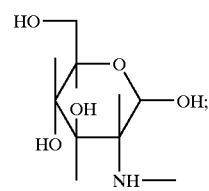
(1b)

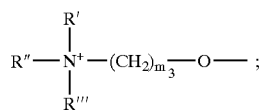
(1c)

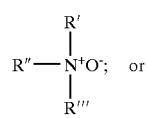
(1d)

or

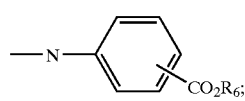
(1e)

wherein

R', R" and R'" are each independently of the others $C_1$–$C_{14}$alkyl which is unsubstituted or substituted by one or more OH groups;

$R_6$ is hydrogen; M; $C_1$–$C_5$alkyl; or a radical of formula —$(CH_2)_{m_2}$—O—$T_1$;

M is a metal cation;

$T_1$ is hydrogen; or $C_1$–$C_8$alkyl;

m is 0 or 1;

$m_2$ is from 1 to 4; and $m_3$ is from 2 to 14.

3. A method according to claim 1, wherein the organic UV filters are chosen from triazine derivatives of formula

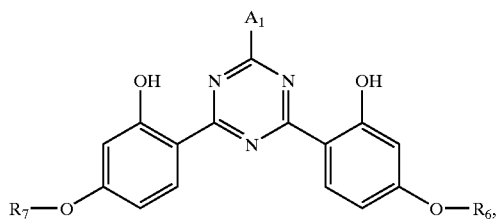
(2)

wherein $R_7$ and $R_8$ are each independently of the other $C_1$–$C_{18}$alkyl; $C_2$–$C_{18}$alkenyl; a radical of formula —$CH_2$—$CH(-OH)$—$CH_2$—O—$T_1$; or $R_7$ and $R_8$ are a radical of formula

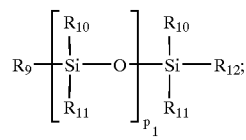
(2a)

$R_9$ is a direct bond; a straight-chain or branched $C_1$–$C_4$alkylene radical or a radical of formula —$C_{m_1}H_{2m_1}$—O—;

$R_{10}$, $R_{11}$ and $R_{12}$ are each independently of the others $C_1$–$C_{18}$alkyl; $C_1$–$C_{18}$alkoxy or a radical of formula

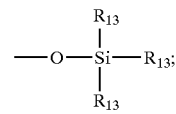

$R_{13}$ is $C_1$–$C_5$alkyl;

$m_1$ is from 1 to 4;

$p_1$ is from 0 to 5;

$A_1$ is a radical of formula

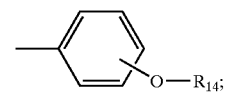
(2b)

(2c)

or

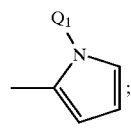
(2d)

$R_{14}$ is hydrogen; $C_1$–$C_{10}$alkyl, —$(CH_2CHR_{16}$—O$)_{n_1}$—$R_{15}$; or a radical of formula —$CH_2$—$CH(-OH)$—$CH_2$—O—$T_1$;

$R_{15}$ is hydrogen; M; $C_1$–$C_5$alkyl; or a radical of formula —$(CH_2)_{m_2}$—O—$(CH_2)_{m_3}$—$T_1$;

$R_{16}$ is hydrogen; or methyl;

$T_1$ is hydrogen; or $C_1$–$C_8$alkyl;

$Q_1$ is $C_1$–$C_{18}$alkyl;

M is a metal cation;

$m_2$ and $m_3$ are each independently of the other from 1 to 4; and $n_1$ is from 1 to 16.

4. A method according to claim 1, wherein the organic UV filters are chosen from triazine derivatives of formula

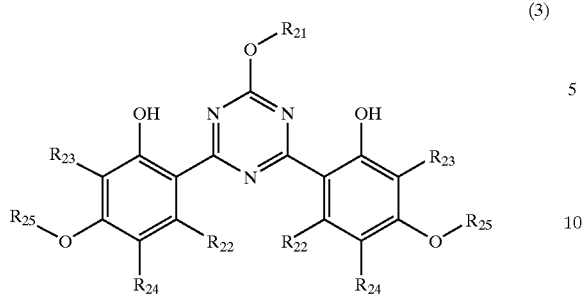 (3)

wherein
$R_{21}$ is $C_1$–$C_{30}$alkyl; $C_2$–$C_{30}$alkenyl; $C_5$–$C_{12}$cycloalkyl unsubstituted or mono- or poly-substituted by $C_1$–$C_5$alkyl; $C_1$–$C_5$alkoxy-$C_1$–$C_{12}$alkyl; amino-$C_1$–$C_{12}$alkyl; $C_1$–$C_5$monoalkylamino-$C_1$–$C_{12}$alkyl; $C_1$–$C_5$dialkylamino-$C_1$–$C_{12}$alkyl; a radical of formula

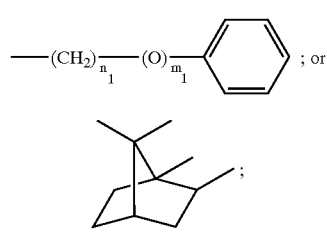 ; or (3a)

(3b)

wherein
$R_{22}$, $R_{23}$ and $R_{24}$ are each independently of the others hydrogen, —OH; $C_1$–$C_{30}$alkyl, $C_2$–$C_{30}$alkenyl,
$R_{25}$ is hydrogen; or $C_1$–$C_5$alkyl;
$m_1$ is 0 or 1; and
$n_1$ is from 1 to 5.

5. A method according to claim 1, wherein the organic UV filters are chosen from triazine derivatives of formula

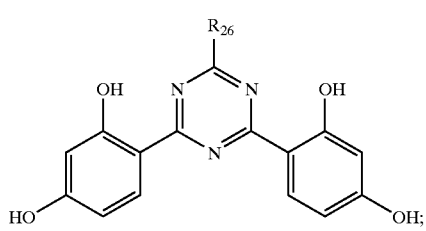 (4)

wherein
$R_{26}$ is

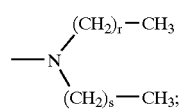

and
r and s are each independently of the other from 0 to 20.

6. A method according to claim 1, wherein the organic UV filters are chosen from triazine derivatives of formula

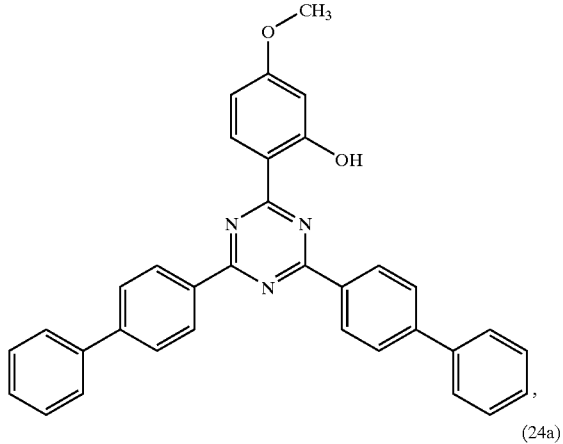 (20a)

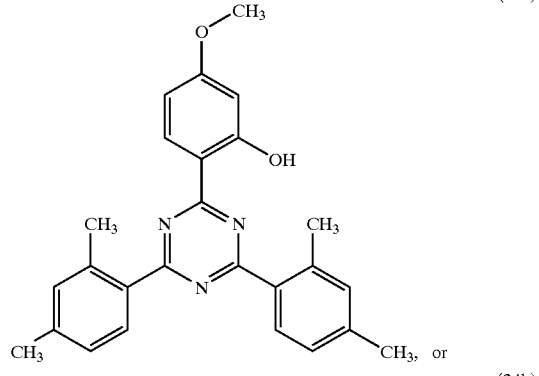 (24a)

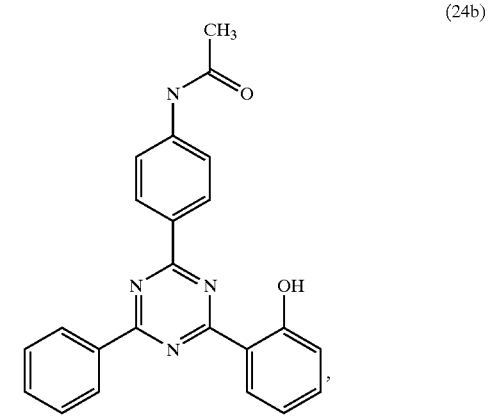 (24b)

7. A method according to claim 1, wherein the organic UV filters are chosen from triazine derivatives of formula

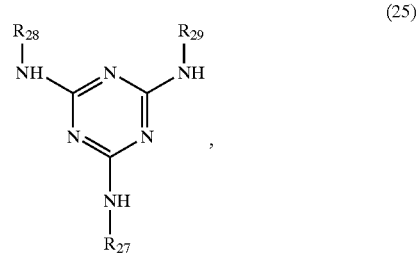 (25)

wherein
$R_{27}$, $R_{28}$ and $R_{29}$ are each independently of the others a radical of formula

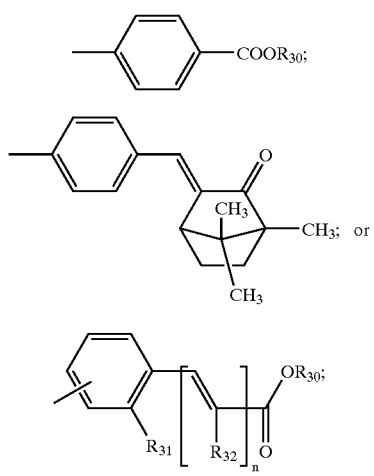
(25a)
(25b)
(25c)

$R_{30}$ is hydrogen; an alkali metal; or an ammonium group —$N(R_{33})_4$, $R_{33}$ is hydrogen, $C_1$–$C_5$alkyl; or a polyoxyethylene radical that has from 1 to 10 ethylene oxide units and the terminal OH group is optionally etherified with a $C_1$–$C_5$alcohol;

$R_{31}$ is hydrogen; —OH; or $C_1$–$C_6$alkoxy;

$R_{32}$ is hydrogen or —COOR$_{30}$; and n is 0 or 1.

8. A method according to claim 1, wherein the organic UV filters are chosen from benzotriazole derivatives of formula

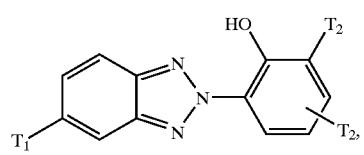
(26)

wherein $T_1$ is $C_1$–$C_5$alkyl or hydrogen; and $T_2$ is $C_1$–$C_5$alkyl or phenyl-substituted $C_1$–$C_5$alkyl.

9. A method according to claim 1, wherein the organic UV filters are chosen from benzotriazole derivatives of formula

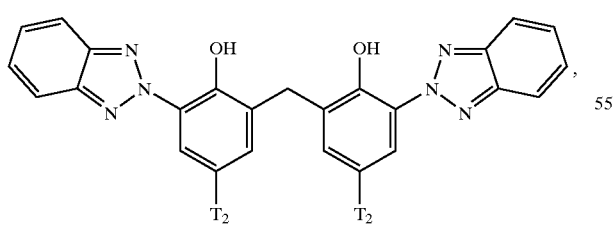
(28)

wherein $T_2$ is $C_1$–$C_4$alkyl, isooctyl, or phenyl-substituted $C_1$–$C_5$alkyl.

10. A method according to claim 1, wherein the Fischer base aldehydes correspond to formula

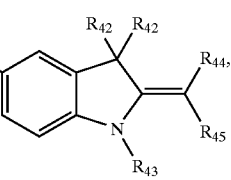
(32)

wherein $R_{41}$ is hydrogen; $C_1$–$C_5$alkyl; $C_1$–$C_{18}$alkoxy; or halogen;

$R_{42}$ is $C_1$–$C_8$alkyl; $C_5$–$C_7$cycloalkyl; or $C_6$–$C_{10}$aryl;

$R_{43}$ is $C_1$–$C_{18}$alkyl or a radical of formula

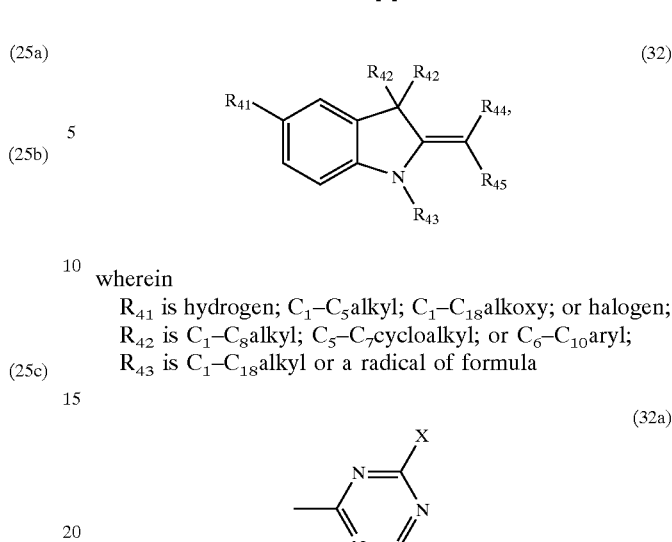
(32a)

$R_{44}$ is hydrogen; or a radical of formula

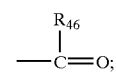

$R_{45}$ is

$C_1$–$C_{18}$alkoxy or a radical of formula

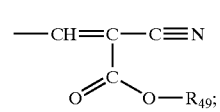
(32b)

$R_{46}$ and $R_{47}$ are each independently of the other hydrogen; or $C_1$–$C_5$alkyl;

$R_{48}$ is hydrogen; $C_1$–$C_5$alkyl; $C_5$–$C_7$cycloalkyl; phenyl; phenyl-$C_1$–$C_3$alkyl;

$R_{49}$ is $C_1$–$C_{18}$alkyl;

X is halogen; a radical of formula

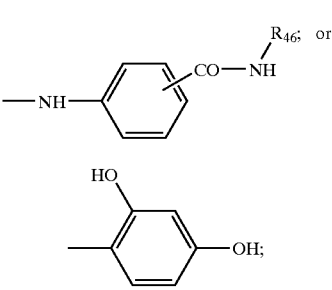
(32c)

(32d)

and n is 0 or 1.

11. A method according to claim 1, wherein the organic UV filters are chosen from compounds of formula

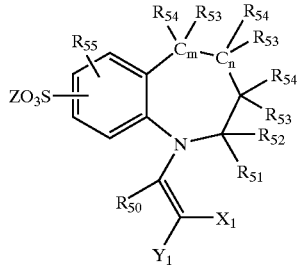

(33)

wherein
- $R_{50}$, $R_{51}$, $R_{52}$, $R_{53}$, $R_{54}$ are each independently of the others hydrogen, $C_1$–$C_8$alkyl or $C_5$–$C_{10}$cycloalkyl;
- $R_{55}$ is hydrogen; $C_1$–$C_8$alkyl; $C_5$–$C_{10}$cycloalkyl; hydroxyl; $C_1$–$C_8$alkoxy; $COOR_{56}$; or $CONR_{57}R_{58}$;
- $R_{56}$, $R_{57}$ and $R_{58}$ are each independently of the others hydrogen or $C_1$–$C_6$alkyl;
- X and Y are each independently of the other hydrogen, —CN; $CO_2R_{59}$; $CONR_{59}R_{60}$; or $COR_{59}$;
- it being possible for the radicals X and Y additionally to be a $C_1$–$C_8$alkyl radical, a $C_5$–$C_{10}$cycloalkyl radical or a heteroaryl radical having 5 or 6 ring atoms, it also being possible for X and Y or
- $R_{50}$ together with one of the radicals X and Y to be the radical for completing a 5- to 7-membered ring which may contain up to 3 hetero atoms, it being possible for the ring atoms to be substituted by exocyclically double-bonded oxygen and/or by $C_1$–$C_8$alkyl and/or by $C_5$–$C_{10}$cycloalkyl radicals and/or to contain C=C double bonds;
- Z is hydrogen; ammonium; an alkali metal ion; or the cation of an organic nitrogen base used for neutralisation of the free acid group,
- $R_{59}$ and $R_{60}$ are each independently of the other hydrogen, $C_1$–$C_8$alkyl or $C_5$–$C_{10}$cycloalkyl; and
- n and m are each independently of the other 0 or 1.

12. A process for the preparation of mixtures of the organic UV filters suitable for the method defined in claim 1, wherein the UV filters, which are in micronised form, are intimately mixed together.

13. A process for the preparation of mixtures of the organic UV filters suitable for the method defined in claim 1, wherein the organic UV filters are micronised in the form of mixtures of at least two single substances.

14. A proces for the preparation of mixtures of the organic UV filters suitable for the method defined in claim 1, wherein at least two single substances are melted together, the melt is cooled and the resulting composite is then subjected to a micronisation process.

15. A composite, obtained by melting together an organic UV filter as defined claim 1.

16. A composite according to claim 15, wherein an inorganic pigment is additionally incorporated into the mixture.

17. A composite according to claim 16, wherein the inorganic pigments are selected from $TiO_2$, ZnO, iron oxides, mica and titanium or zinc salts of organic acids.

18. A composite, obtained by melting together at least two of the organic UV filters defined in claim 1 and at least one antioxidant.

19. A composite according to claim 18, wherein the antioxidant is selected from tocopherols, ellagic acid, propyl gallate, butylated hydroxytoluene, butylated hydroxyanisole, 2,4,6-tris(3,5-di-tert-butyl-4-hydroxybenzyl)mesitylene, tetrakis[methylene-3-(3',5'-di-tert-butyl-4'-hydroxyphenyl)propionate]methane, the compound of formula

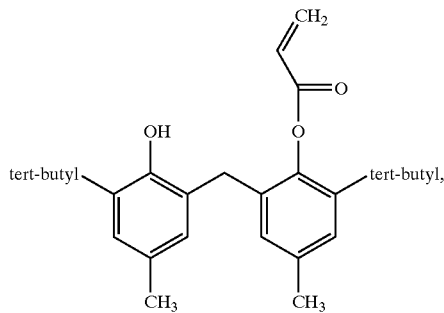

the compound of formula

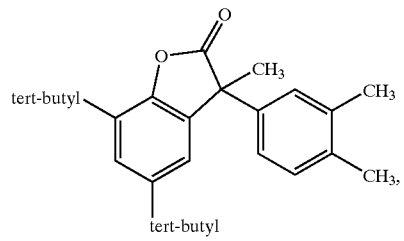

vanillin, ubiquinone, ferulic acid, ferulic acid derivatives, rutinic acid, rutinic acid derivatives; urocanic acid, urocanic acid derivatives; and propolis.

20. A composite, obtained by melting together an organic UV filter as defined in claim 1 and at least one antioxidant, and one or more inorganic pigments.

21. A method according to claim 1, herein a cationic or anionic compound is incorporated into the mixture.

22. A composite, obtained by melting together an organic UV filter as defined in claim 1 and at least one cationic or anionic compound.

23. A method according to claim 1, wherein a pharmaceutical or cosmetic active ingredient is additionally incorporated into the mixture.

24. A cosmetic formulation, comprising an organic UV filter as defined in claim 1, optionally one or more compounds selected from the group consisting of antioxidants, inorganic pigments and cationic or anionic compounds, and also a cosmetically acceptable carrier or adjuvant.

25. A cosmetic formulation according to claim 24, which additionally comprises an oil-soluble, non-micronised UV filter.

26. A pharmaceutical formulation, comprising an organic UV filter as defined in claim 1, optionally one or more compounds selected from antioxidants, inorganic pigments and cationic or anionic compounds, and also a pharmaceutically acceptable carrier or adjuvant.

* * * * *